United States Patent
D'Andrea et al.

(10) Patent No.: US 10,526,402 B2
(45) Date of Patent: *Jan. 7, 2020

(54) ANTI-TGF-BETA ANTIBODY FOR THE TREATMENT OF FANCONI ANEMIA

(71) Applicant: Dana-Farber Cancer Institute, Inc., Boston, MA (US)

(72) Inventors: Alan D'Andrea, Winchester, MA (US); Kalindi Parmar, Arlington, MA (US); Haojian Zhang, Shrewsbury, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/553,930

(22) PCT Filed: Feb. 25, 2016

(86) PCT No.: PCT/US2016/019626
§ 371 (c)(1),
(2) Date: Aug. 25, 2017

(87) PCT Pub. No.: WO2016/138301
PCT Pub. Date: Sep. 1, 2016

(65) Prior Publication Data
US 2018/0051075 A1 Feb. 22, 2018

Related U.S. Application Data

(60) Provisional application No. 62/120,596, filed on Feb. 25, 2015.

(51) Int. Cl.
| A61K 39/395 | (2006.01) |
| C07K 16/22 | (2006.01) |
| A61K 39/00 | (2006.01) |

(52) U.S. Cl.
CPC .......... *C07K 16/22* (2013.01); *A61K 39/3955* (2013.01); *A61K 2039/505* (2013.01); *A61K 2039/54* (2013.01); *A61K 2039/545* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| 2014/0328860 A1* | 11/2014 | Scandura | ............. | C07K 14/495 424/158.1 |
| 2018/0071330 A1 | 3/2018 | D'Andrea et al. | | |

FOREIGN PATENT DOCUMENTS

| WO | WO 2014/110020 A1 | 7/2014 |
| WO | WO 2016/138300 A1 | 9/2014 |

OTHER PUBLICATIONS

Peffault de Latour et al., Blood, 2013, vol. 122(26):4279-4286.*
Rose et al., Pediatr. Blood Cancer, 2014, vol. 61(1):11-19.*
Adamo, A. et al., "Preventing nonhomologous end joining suppresses DNA repair defects of Fanconi anemia," Mol Cell 39, 25-35 (2010).
Benazet, J.D. et al., "Smad4 is required to induce digit ray primordia and to initiate the aggregation and differentiation of chondrogenic progenitors in mouse limb buds," Development 139, 4250-4260 (2012).
Brenet, F. et al., "TGFβ restores hematopoietic homeostasis after myelosuppressive chemotherapy," J Exp Med 210, 623-639 (2013).
Bunting, S.F. & Nussenzweig, A., "Dangerous liaisons: Fanconi anemia and toxic nonhomologous end joining in DNA crosslink repair," Mol Cell 39, 164-166 (2010).
Ceccaldi, R., "Bone marrow failure in Fanconi anemia is triggered by an exacerbated p53/p21 DNA damage response that impairs hematopoietic stem and progenitor cells," Cell Stem Cell 11, 36-49 (2012).
Chan, K.L. et al., "Replication stress induces sister-chromatid bridging at fragile site loci in mitosis," Nat Cell Biol 11, 753-760 (2009).
Cron, K.R. et al., "Proteasome inhibitors block DNA repair and radiosensitize non-small cell lung cancer," PLoS One 8, e73710 (2013).
Crossan, G.P. et al., "Disruption of mouse Slx4, a regulator of structure-specific nucleases, phenocopies Fanconi anemia," Nature Genetics 43, 147-152 (2011).
Deans, A.J. & West, S.C., "DNA interstrand crosslink repair and cancer," Nat Rev Cancer 11, 467-480 (2011).
Dufour, C. et al., "TNF-alpha and IFN-gamma are overexpressed in the bone marrow of Fanconi anemia patients and TNF-alpha suppresses erythropoiesis in vitro," Blood 102, 2053-2059 (2003).
Epperly, M.W. et al., "Increased longevity of hematopoiesis in continuous bone marrow cultures and adipocytogenesis in marrow stromal cells derived from Smad3(-/-) mice," Exp Hematol 33, 353-362 (2005).
Garaycoechea, J.I. et al., "Genotoxic consequences of endogenous aldehydes on mouse haematopoietic stem cell function," Nature 489, 571-575 (2012).
Grafe, I. et al., "Excessive transforming growth factor-beta signaling is a common mechanism in osteogenesis imperfect," Nature Medicine 20, 670-675 (2014).
Hanoun, M. et al., "Acute myelogenous leukemia-induced sympathetic neuropathy promotes malignancy in an altered hematopoietic stem cell niche," Cell Stem Cell 15, 365-375 (2014).
Ichida, J.K. et al., "A small-molecule inhibitor of tgf-Beta signaling replaces sox2 in reprogramming by inducing nanog," Cell Stem Cell 5, 491-503 (2009).

(Continued)

*Primary Examiner* — Xiaozhen Xie
(74) *Attorney, Agent, or Firm* — Cooley LLP; Ivor R. Elrifi; Cynthia A. Kozakiewicz

(57) ABSTRACT

The present invention provides methods of treating, preventing or delaying the onset of bone marrow failure in Fanconi Anemia patients comprising administering to the patient a composition comprising a neutralizing anti-TGF-beta antibody, e.g. fresolimumab or 1D11.

15 Claims, 23 Drawing Sheets

Figure 1A:
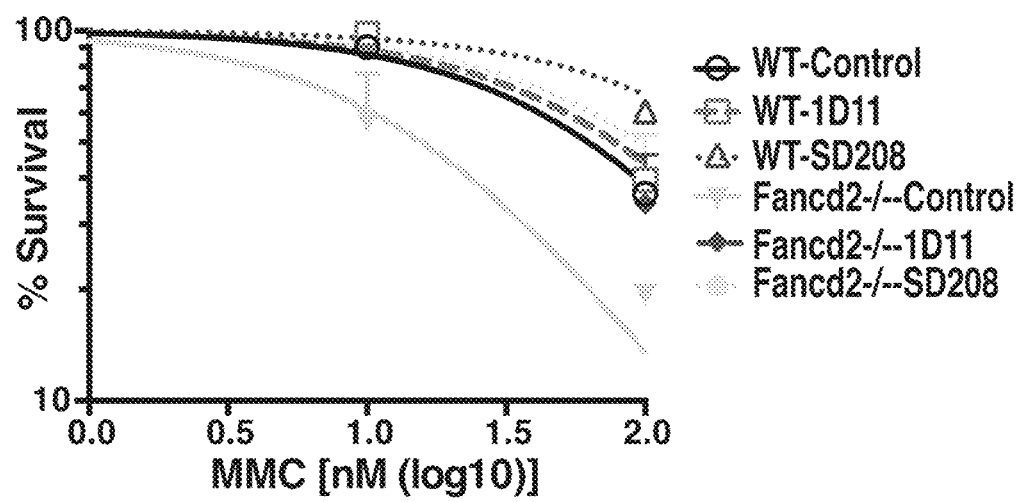
Figure 1A:
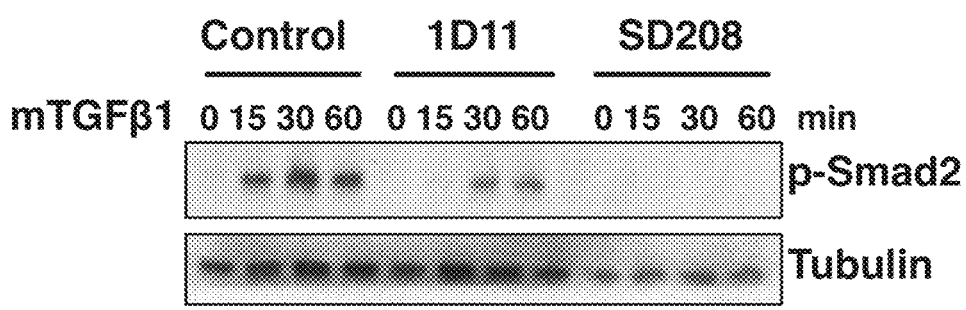

Specification includes a Sequence Listing.

(56) References Cited

OTHER PUBLICATIONS

Ikushima, H. & Miyazono, K., "TGFbeta signalling: a complex web in cancer progression," Nat Rev Cancer 10, 415-424 (2010).
Ito, K. et al., "Reactive oxygen species act through p38 MAPK to limit the lifespan of hematopoietic stem cells," Nature Medicine 12, 446-451 (2006).
Jessen, W.J. et al., "MEK inhibition exhibits efficacy in human and mouse neurofibromatosis tumors," J Clin Invest 123, 340-347 (2013).
Jinnin, M. et al., "Characterization of SIS3, a novel specific inhibitor of Smad3, and its effect on transforming growth factor-beta1-induced extracellular matrix expression," Molecular Pharmacology 69, 597-607 (2006).
Kennedy, R.D. et al., "Fanconi anemia pathway-deficient tumor cells are hypersensitive to inhibition of ataxia telangiectasia mutated," J Clin Invest 117, 1440-1449 (2007).
Kirshner, J. et al., "Inhibition of transforming growth factor-beta1 signaling attenuates ataxia telangiectasia mutated activity in response to genotoxic stress," Cancer Res 66, 10861-10869 (2006).
Kottemann, M.C. & Smogorzewska, A., "Fanconi anaemia and the repair of Watson and Crick DNA crosslinks," Nature 493, 356-363 (2013).
Krause, D.S. et al., "Differential regulation of myeloid leukemias by the bone marrow microenvironment," Nature Medicine 19, 1513-1517 (2013).
Langevin, F. et al, "Fancd2 counteracts the toxic effects of naturally produced aldehydes in mice," Nature 475, 53-58 (2011).
Li, J. et al., "TNF-alpha induces leukemic clonal evolution ex vivo in Fanconi anemia group C murine stem cells," J Clin Invest 117, 3283-3295 (2007).
Li, Y. et al., "Mesenchymal stem/progenitor cells promote the reconstitution of exogenous hematopoietic stem cells in Fancg-/- mice in vivo," Blood 113, 2342-2351 (2009).
Lin, T. et al., "A chemical platform for improved induction of human iPSCs," Nat Methods 6, 805-808 (2009).
Mansour, W.Y. et al., "Hierarchy of nonhomologous end-joining, single-strand annealing and gene conversion at site-directed DNA double-strand breaks," Nucleic Acids Research 36, 4088-4098 (2008).
McKenna, D.J. et al., "Modification of the alkaline Comet assay to allow simultaneous evaluation of mitomycin C-induced DNA crosslink damage and repair of specific DNA sequences in RT4 cells," DNA Repair (Amst) 2, 879-890 (2003).
Milyavsky, M. et al., "A distinctive DNA damage response in human hematopoietic stem cells reveals an apoptosis-independent role for p53 in self-renewal," Cell Stem Cell 7, 186-197 (2010).
Mohrin, M. et al.,"Hematopoietic stem cell quiescence promotes error-prone DNA repair and mutagenesis," Cell Stem Cell 7, 174-185 (2010).
Naim, V. & Rosselli, F., "The FANC pathway and BLM collaborate during mitosis to prevent micro-nucleation and chromosome abnormalities," Nat Cell Biol 11, 761-768 (2009).
Nakanishi, K. et al., "Human Fanconi anemia monoubiquitination pathway promotes homologous DNA repair," Proceedings of the National Academy of Sciences of the United States of America 102, 1110-1115 (2005).
Niedernhofer, L.J., "DNA repair is crucial for maintaining hematopoietic stem cell function," DNA Repair (Amst) 7, 523-529 (2008).
Pace, P. et al.,"Ku70 corrupts DNA repair in the absence of the Fanconi anemia pathway," Science 329, 219-223 (2010).
Pang, Q. & Andreassen, P.R., "Fanconi anemia proteins and endogenous stresses," Mutat Res 668, 42-53 (2009).
Pang, Q. et al., "FANCC interacts with Hsp70 to protect hematopoietic cells from IFN-gamma/TNF-alpha-mediated cytotoxicity," The EMBO Journal 20, 4478-4489 (2001).
Pang, Q. et al., "The Fanconi anemia protein FANCC binds to and facilitates the activation of STAT1 by gamma interferon and hematopoietic growth factors," Molecular and Cellular Biology 20, 4724-4735 (2000).
Parmar, K. et al., "Hematopoietic stem cell defects in mice with deficiency of Fancd2 or Usp1," Stem Cells 28, 1186-1195 (2010).
Pulliam-Leath, A.C. et al., "Genetic disruption of both Fancc and Fancg in mice recapitulates the hematopoietic manifestations of Fanconi anemia," Blood 116, 2915-2920 (2010).
Raaijmakers, M.H. et al., "Bone progenitor dysfunction induces myelodysplasia and secondary leukaemia," Nature 464, 852-857 (2010).
Ruzankina, Y. et al., "Deletion of the developmentally essential gene ATR in adult mice leads to age-related phenotypes and stem cell loss," Cell Stem Cell 1, 113-126 (2007).
Seita, J. et al., "Differential DNA damage response in stem and progenitor cells," Cell Stem Cell 7, 145-147 (2010).
Shimamura, A. & Alter, B.P., Pathophysiology and management of inherited bone marrow failure syndromes, Blood Reviews 24, 101-122 (2010).
Tulpule, A. et al., "Knockdown of Fanconi anemia genes in human embryonic stem cells reveals early developmental defects in the hematopoietic lineage," Blood 115, 3453-3462 (2010).
Vinciguerra, P. et al., "Cytokinesis failure occurs in Fanconi anemia pathway-deficient murine and human bone marrow hematopoietic cells," J Clin Invest 120, 3834-3842 (2010).
Wu, J.H. & Jones, N.J., "Assessment of DNA interstrand crosslinks using the modified alkaline comet assay," Methods Mol Biol 817, 165-181 (2012).
Zhang, Q.S. et al., "Fancd2-/- mice have hematopoietic defects that can be partially corrected by resveratrol," Blood 116, 5140-5148 (2010).
Zhou, L. et al., "Reduced SMAD7 leads to overactivation of TGF-beta signaling in MDS that can be reversed by a specific inhibitor of TGF-beta receptor I kinase," Cancer Res 71, 955-963 (2011).
Zingariello, M. et al., "Characterization of the TGF-beta1 signaling abnormalities in the Gata1low mouse model of myelofibrosis," Blood 121, 3345-3363 (2013).
Brown, C. B. et al., "Antibodies to the Type II TGFβ Receptor Block Cell Activation and Migration during Atrioventricular Cushion Transformation in the Heart," Developmental Biology, 174:248-257 (1996).
Kee, Y. et al., "Molecular pathogenesis and clinical management of Faconi anemia," Journal of Clinical Investigation, 122(11):3799-3806 (2002).
Anonymous, "Monoclonal Anti-CD314-APC antibody produced in mouse clone 1D11, purified immunoglobulin, buffered aqueous solution", www.sigmaaldrich.com/catalog/product /sigma/sab4700720?lang_de ion-De, Jan. 1, 2016.
D'Andrea, Alan D. Ed—Humphries R. Keith, "Fanconi Anemia and Bone Marrow Failure", Experimental Hematology, Aug. 28, 2015, vol. 43, No. 9, Supplement 1, p. S40.
Ganapathy Vidya, et al., "Targeting the Transforming Growth Factor-1 pathway inhibits human basal-like breat cancer metastasis", Molecular Cancer, Biomed Central, London, GB, May 26, 2010, vol. 9, No. 1, p. 122.
Zhang Haojian, et al., "TGF-beta Pathway Inhibition Rescues the Function of Hematopoietic Stem and Progenitor Cells Derived from Patients with Faconi Anemia", Blood, & 57th Annual Meeting of the American-Society-of-Hematology, Dec. 2015, vol. 126, No. 23, Abstract.
Zhang Haojian, et al.,"Bone Marrow Failure in Fanconi Anemia from Huperactive TGF-beta Signaling", Blood, & 56th Annual Meeting of American-Society-Of-Hematology, Dec. 2014, vol. 124, No. 21, Abstract.
Mario E. Lacouture, et al., "Cutaneous keratoacanthomas/squamous cell carcinomas associated with neutralization of transforming growth factor [beta] by the monoclonal antibody fresolimumab (GC1008)", Cancer Immunology and Immunotherapy, Jan. 13, 2015, vol. 64, No. 4, pp. 437-446.
John C. Morris, et al., "Phase I Study of GC1008 (Fresolimumab): A Human Anti-Transforming Growth Factor-Beta (TGF[beta]) Monoclonal Antibody in Patients with Advanced Malignant Melanoma or Renal Cell Carcinoma", PLOS One, Mar. 11, 2014, vol. 9, No. 3, p. e90353, 11 Pages.

(56) References Cited

OTHER PUBLICATIONS

Sofie Singbrant Soderberg, et al., "Complex and Context Dependent Regulation of Hematopoiesis by TGF-[beta] Superfamily Signaling", Annals of the New York Academy of Sciences, Sep. 1, 2009, pp. 55-69, vol. 1176, No. 1.

Svahn Johanna, et al., "p38 mitogen-activated protein kinase inhibition enhances in vitro erythropoiesis of Fanconi anemia, complementation group A-deficient bone marrow cells", Experimental Hematology, Dec. 19, 2014, vol. 43, No. 4, pp. 295-299.

Younghoon Kee et al., "Molecular pathogenesis and clinical management of Faconi anemia", Jounal of Clinical Investigation, Nov. 1, 2002, vol. 122, No. 11, pp. 3799-3806.

Chen Zean et al., "DNA Cross-Linking Agent Sensitivity of Fanconi Anemia (FA) Cells Is Preserved in Double Knockout (DKO) SMAD3(-/-)Fancd2(-/-) Mouse Cell Lines", Dec. 2015, Abstract, Blood, 2015, vol. 126(23) : 4799.

Bagby Grover C., "The Role of Innate Immune Dysfunction in Inherited Bone Marrow Failure", Blood & 56th Annual Meeting of the American-Society-of-Hematology; Dec. 2014, vol. 124, No. 21.

Falvello, Virginia, et al., "Production of TGF-beta Is Decreased in the Bone Marrow of Double Knockeout (DKO) SMAD3(-/-) Fancd2 (-/-) Mice", Blood & 57th Annual Meeting of the American-Society-of-Hematology Dec. 2015, vol. 126, No. 23.

Chen Katherine et al., "Radiosensitivity of fANCD2(-/-) mouse bone marrow stromal cells is altered by Abrogation of TGF-beta Signaling", Dec. 2015, Blood & 57th Annual Meeting of the American-Society-of-Hematology, vol. 126, No. 23.

Shah, A H, et al., "Suppression of tumor metastasis by blockade of transforming growth factor beta signaling in bone marrow cells through a retroviral-mediated gene therapy in mice", Cancer Research, American Associateion for Cancer Research, US, Dec. 15, 2002, vol. 62, No. 24, pp. 7136-7138.

L. Zhou, et al., "Inhibition of the TGF-receiptor I kinase promotes hematopoiesis in MDS", Blood, Oct. 15, 2008, vol. 112, No. 8, pp. 3434-3443.

* cited by examiner

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence

```
<220> FEATURE:
<223> OTHER INFORMATION: Artificial polynucleotide

<400> SEQUENCE: 1
cagctcctca tcgtgttggt g                                              21

<210> SEQ ID NO 2
<211> LENGTH: 22
<212> TYPE: DNA
<213> ORGANISM: Artificial Sequence
<220> FEATURE:
<223> OTHER INFORMATION: Artificial polynucleotide

<400> SEQUENCE: 2
gcacatacaa atggcctgtc tc                                             22

<210> SEQ ID NO 3
<211> LENGTH: 19
<212> TYPE: DNA
<213> ORGANISM: Artificial Sequence
<220> FEATURE:
<223> OTHER INFORMATION: Artificial polynucleotide

<400> SEQUENCE: 3
cacgcagaac gtgaacacc                                                 19

<210> SEQ ID NO 4
<211> LENGTH: 21
<212> TYPE: DNA
<213> ORGANISM: Artificial Sequence
<220> FEATURE:
<223> OTHER INFORMATION: Artificial polynucleotide

<400> SEQUENCE: 4
ggcagtagat aacgtgaggg a                                              21

<210> SEQ ID NO 5
<211> LENGTH: 20
<212> TYPE: DNA
<213> ORGANISM: Artificial Sequence
<220> FEATURE:
<223> OTHER INFORMATION: Artificial polynucleotide

<400> SEQUENCE: 5
tggatttgga cgcattggtc                                                20

<210> SEQ ID NO 6
<211> LENGTH: 21
<212> TYPE: DNA
<213> ORGANISM: Artificial Sequence
<220> FEATURE:
<223> OTHER INFORMATION: Artificial polynucleotide

<400> SEQUENCE: 6
tttgcactgg tacgtgttga t                                              21

<210> SEQ ID NO 7
<211> LENGTH: 20
<212> TYPE: DNA
<213> ORGANISM: Artificial Sequence
<220> FEATURE:
<223> OTHER INFORMATION: Artificial polynucleotide

<400> SEQUENCE: 7
aaggcaggag aattgcttga                                                20
```

```
<210> SEQ ID NO 8
<211> LENGTH: 20
<212> TYPE: DNA
<213> ORGANISM: Artificial Sequence
<220> FEATURE:
<223> OTHER INFORMATION: Artificial polynucleotide

<400> SEQUENCE: 8
ccttcacctt ctgccatgat                                             20

<210> SEQ ID NO 9
<211> LENGTH: 19
<212> TYPE: DNA
<213> ORGANISM: Artificial Sequence
<220> FEATURE:
<223> OTHER INFORMATION: Artificial polynucleotide

<400> SEQUENCE: 9
caagggaggg tttcaacag                                              19

<210> SEQ ID NO 10
<211> LENGTH: 22
<212> TYPE: DNA
<213> ORGANISM: Artificial Sequence
<220> FEATURE:
<223> OTHER INFORMATION: Artificial polynucleotide

<400> SEQUENCE: 10
tgagcactta ctggtcaatt cg                                          22
```

ANTI-TGF-BETA ANTIBODY FOR THE TREATMENT OF FANCONI ANEMIA

RELATED APPLICATIONS

This application is a National Stage Application, filed under 35 U.S.C. § 371, of International Application No. PCT/US2016/019626, filed on Feb. 25, 2016, which claims priority to, and the benefit of, U.S. Provisional Application No. 62/120,596, filed on Feb. 25, 2015, the contents of each of which are incorporated herein by reference in their entireties.

INCORPORATION BY REFERENCE OF SEQUENCE LISTING

The contents of the text file named "DFCI-107_N01US Sequence Listing.txt", which was created on Aug. 24, 2017 and is 2.19 KB in size, are hereby incorporated by reference in their entireties.

FIELD OF THE INVENTION

The present invention relates generally to treating, preventing, or delaying the onset of bone marrow failure associated Fanconi Anemia.

BACKGROUND OF THE INVENTION

Fanconi Anemia (FA) is an autosomal recessive DNA repair disorder characterized by congenital abnormalities, cancer predisposition, and progressive bone marrow failure (BMF). FA is caused by biallelic mutations in one of sixteen FANC genes, the products of which cooperate in the FA/BRCA DNA repair pathway. Although the precise biochemical functions of the FA/BRCA pathway remain unclear, the pathway promotes homologous recombination (HR) repair. The FA/BRCA pathway also regulates cytokinesis, and pathway disruption results in increased binucleate bone marrow cells and apoptosis. FA cells are also uniquely hypersensitive to oxidative stress and apoptotic cytokines, such as IFNγ and TNFα.

BMF of FA patients is attributable to impaired stem cell pool. FA patients develop progressive bone marrow failure during childhood, and frequently require an allogeneic or unrelated donor bone marrow transplant. All blood lineages are deficient in FA patients suggests that the FA pathway regulates the function of hematopoietic stem and progenitor cells (HSPCs). CD34$^+$ cells of FA patients, which are a human stem cell/progenitor cell enriched population, were not only lower in the number, but also exhibited compromised clonogenicity. Similarly, mice with Fanc mutations also displayed reduced numbers of hematopoietic stem cells (HSCs) with impaired reconstitution ability. In addition, the FA pathway also controls hematopoietic development. Knockdown of FANCA and FANCD2 in human embryonic stem cells impaired embryonic hematopoiesis which could be rescued by FA gene complementation. Therefore, these studies link FA pathway with stem cell function.

The mechanism of bone marrow failure in FA remains elusive. A need exist for a better understanding of the mechanism of BMF in FA as well as therapies to treat BMF other than bone marrow transplant.

SUMMARY OF THE INVENTION

The invention provides methods of treating, preventing or delaying the onset of bone marrow failure in a patient having Fanconi Anemia (FA) by administering to the patient a composition comprising fresolimumab, 1D11 or an antigen binding fragment thereof.

The composition is administered before the patient is prepared for a bone marrow transplant, after the patient receives a bone marrow transplant or after the patient is prepared for a bone marrow transplant but prior to the bone marrow transplant.

Alternatively the composition is administered when the patient is having medical crisis, such as an infection. The infection is viral or bacterial. Optionally the method further includes administering androgen therapy or erythropoietin.

The composition is administered at a dose of 0.1 mg/kg to 150 mg/kg. Preferably the composition is administers at a dose of 0.5 mg/kg to 10 mg/kg. More preferably, the composition is administered at a dose of 1 mg/kg to 5 mg/kg.

The composition is administered one to seven times per week. Preferably, the composition is administered three times per week. More preferably the composition is administered two times per week.

The composition is administered for a duration of 1 week to 1 year. Alternatively, the composition is administered for a duration of one to two months. In other embodiments the composition is administered chronically. Preferably, composition is administered intravenously.

Also include in the invention is a method of administering to a patient that has been prepared to receive a bone marrow transplant a composition comprising fresolimumab, 1D11 or an antigen binding fragment thereof.

In another aspect the invention provides a method of expanding hematopoietic stem/progenitor cells comprising contacting a population of hematopoietic stem/progenitor cells with fresolimumab, 1D11 or an antigen binding fragment thereof.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTIONS OF THE DRAWINGS

FIG. 1. TGFβ pathway inhibition corrects impaired stem cell function of FA mice.

A) TGFβ pathway inhibition by 1D11 and SD208 restores MMC resistance of Fancd2−/− stromal cells. Top panel: survival of WT or Fancd2−/− stromal cells in the presence of MMC. Error bars represent s.e.m. Bottom panel: Immunoblot of p-Smad2, showing the inhibition of TGFβ signaling in stromal cells treated by 1D11 and SD208. B) Acetaldehyde sensitivity of Lin− cells, from WT or Fancd2−/− mice, incubated with or without 1D11. C) Colony forming assay, showing acetaldehyde resistance of Fancd2−/− HSCs (CD150+LSK cells) with 1D11 treatment. D) Schematic experimental design of the in vivo engraftment assay, using lentivirus shRNA transduction of Lin− BM cells from WT and Fancd2–/– mice. E) Deletion of Smad3 promotes the engraftment of Fancd2–/– cells (n=5 mice per group).

FIG. 2. Fancd2–/– HSPCs are more sensitive to the suppressive function of TGFβ.

A) Fancd2–/– HSPCs are more sensitive to TGFβ than WT HSPCs. Sorted Lin– cells from WT and Fancd2–/– mice were treated with mTGFβ (0.1, 1, 10 ng/mL). After 5 days culture, LSK cells were counted and analyzed by flow cytometry. Data were shown after normalizing to untreated WT and Fancd2–/– group respectively. B) 1D11 and SD208 rescued the inhibitory effect of mTGFβ on Lin– cell growth. Sorted Lin– cells from WT and Fancd2–/– mice were treated with mTGFβ (1 ng/mL) with or without 1D11 or SD208. Data are shown, after normalizing to untreated WT and Fancd2–/– group respectively. C) Clonogenic assay of WT and Fancd2–/– HSPCs treated with mTGFβ, 1D11 or SD208. D) Hemoglobin levels in MMC treated WT and Fancd2–/– mice, treated with or without 1D11 treatment. E) Red blood cells counts in MMC treated WT and Fancd2–/– mice, treated with or without 1D11 treatment.

Figure 3:
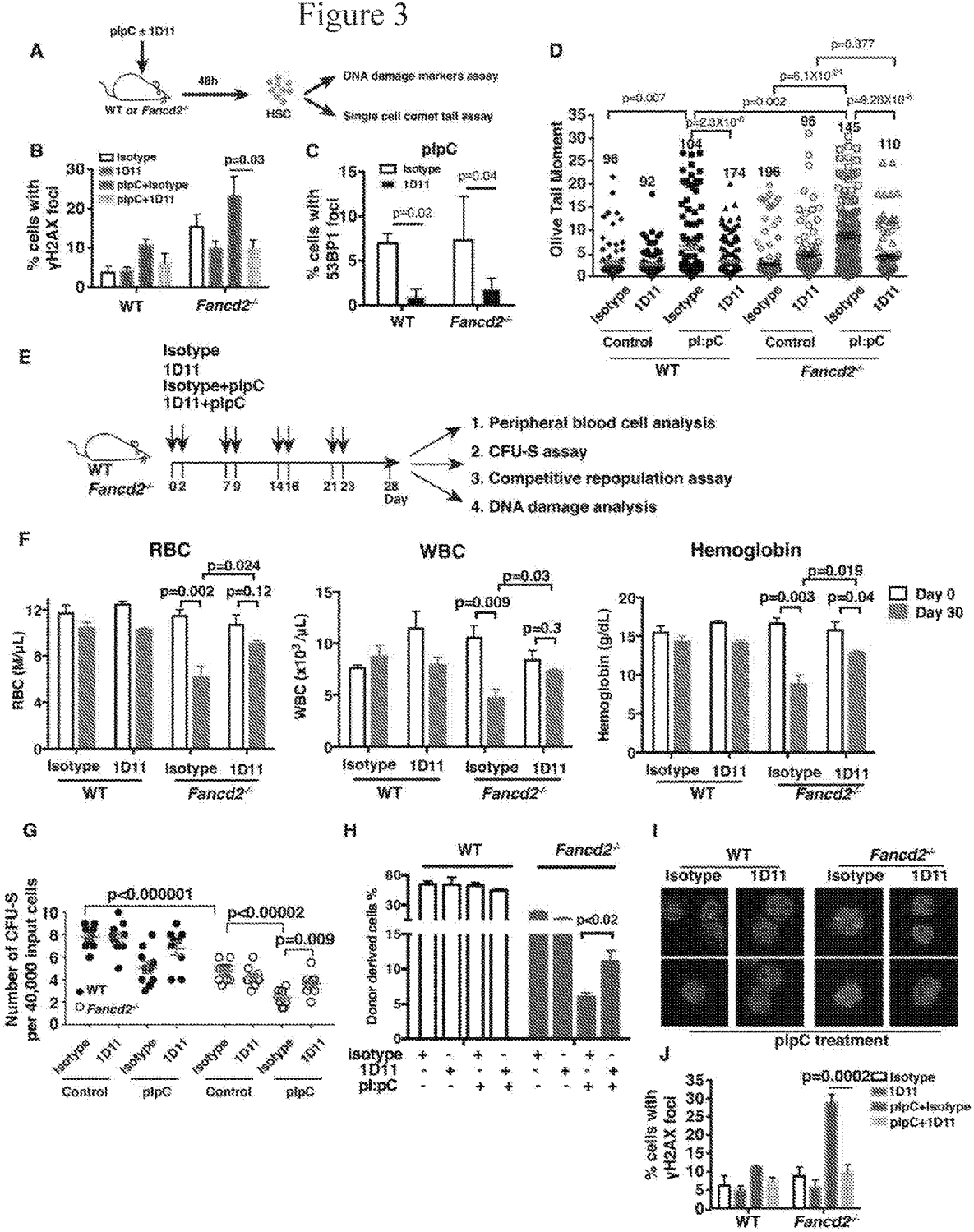

FIG. 3. Inhibition of TGF-β Pathway Rescues Physiological Stress-induced Bone Marrow Failure in FA Mice (A) TGF-β pathway inhibition by 1D11 prevents pI:pC induced DNA damage in HSCs in vivo. WT and Fancd2–/– mice were injected intraperitoneally with pI:pC (5 mg/kg) and 1D11 or isotype control antibody (10 mg/kg). Forty-eight hours after the treatments, HSCs were sorted for DNA damage analysis by immunofluorescence staining or by the single cell comet tail assay. (B) Percentages of HSCs with γH2AX foci) and (C) 53BP1 foci are shown. Hundred to 150 cells were counted for each sample. (D) Olive tail moment in a comet assay demonstrating that 1D11 significantly reduces I:pC induced DNA damage in Fancd2–/– HSCs. Ninety-two to 196 HSCs from each group were scored. (E) Schematic of pI:pC-induced bone marrow failure mouse model. (F) Peripheral blood analysis of pI:pC plus isotype or 1D11-treated WT and Fancd2–/– mice as shown in (E). Red blood cell (RBC) counts, white blood cell counts (WBCs) and hemoglobin levels are shown (n=4-5 mice per group). (G) CFU-S content in the bone marrow of WT or Fancd2–/– mice after four weeks of pI:pC plus isotype or 1D11 treatment as shown in (E). (H) Inhibition of TGF-β pathway rescues pI;pC-mediated functional defects of HSPCs. WT and Fancd2–/– mice were exposed to pI:pC plus isotype or 1D11 for four weeks as shown in (E) and bone marrow cells were transplanted into lethally irradiated recipients (CD45.1) along with 1×105 helper cells (CD45.1). Donor-derived cells (CD45.2) in peripheral blood were analyzed at 4 weeks post transplantation (n=4-5 recipient mice per group). (I, J) 1D11 rescues pI:pC-induced DNA damage in HSPCs. (I) Representative images and (J) quantification of γH2AX foci in HSPCs from WT and Fancd2–/– mice after four weeks treatment with pI:pC plus isotype or 1D11 as shown in (E). Error bars represent s.e.m. See also FIG. 7.

Figure 4:
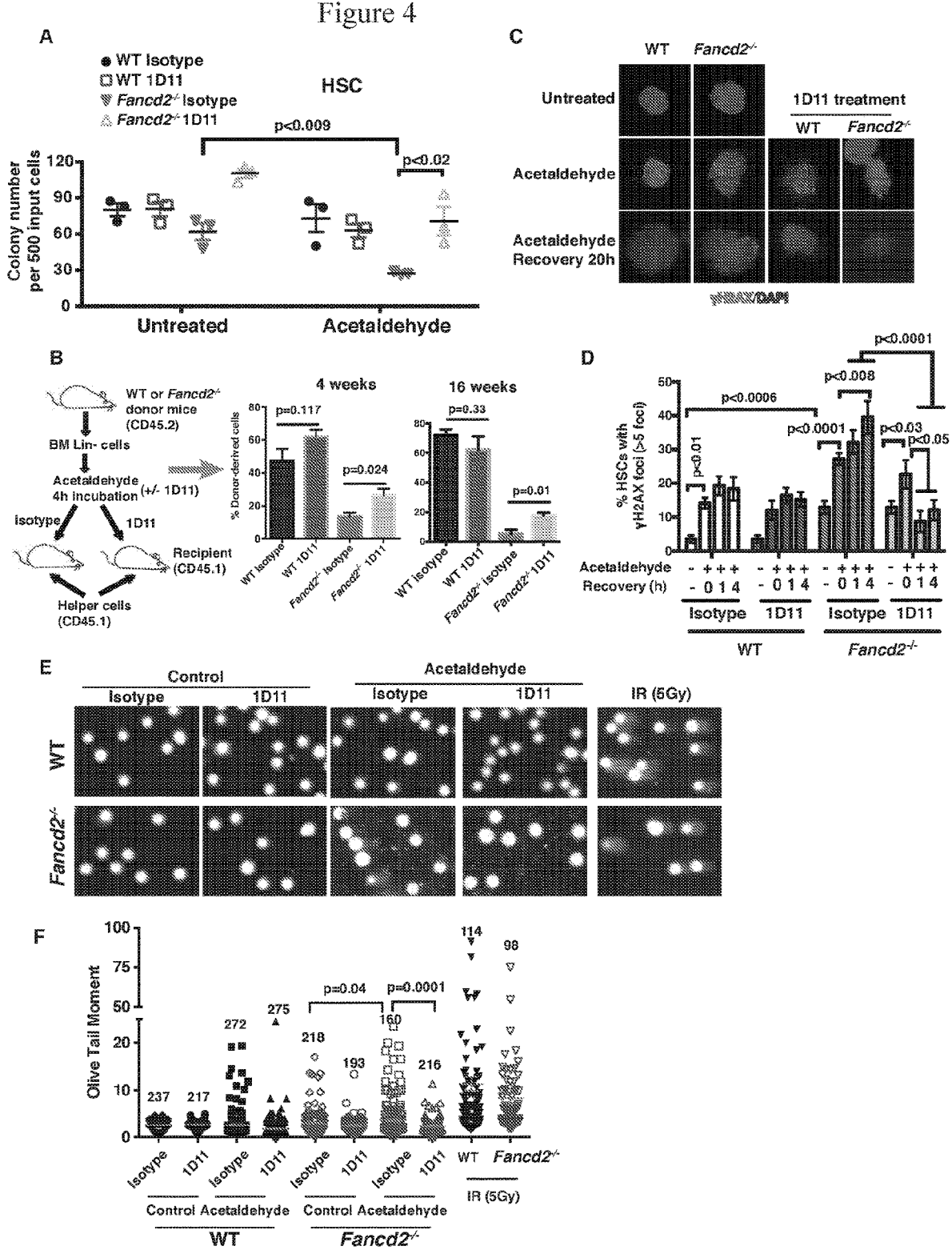

FIG. 4. TGF-β pathway Inhibition Rescues Acetaldehyde-induced Genotoxicity in HSPCs from FA Mice.

(A) Colony forming assay showing acetaldehyde resistance of Fancd2–/– HSCs (CD48-CD150+LSK cells) with 1D11 treatment. HSCs from WT and Fancd2–/– mice were exposed 2 mM acetaldehyde for 4h and then cultured in methycellulose medium containing 10 μg/mL 1D11 or its isotype control antibodies for 10 days. Survival of the hematopoietic progenitors was determined by colony quantification. (B) Inhibition of TGF-β pathway enhances acetaldehyde resistance of HSCs. Lin– cells from bone marrow (BM) of WT and Fancd2–/– mice were pretreated with 1D11 or isotype control antibody for 30 min, followed by exposure to 2 mM acetaldehyde for 4h. After 24h in culture with 1D11 or isotype control antibody, equal numbers of cells were transplanted into lethally irradiated recipients (CD45.1) along with 1×105 helper cells (CD45.1). Donor-derived cells (CD45.2) in peripheral blood were analyzed by flow cytometric analysis at 4 and 16 weeks post transplantation (n=4-5 recipient mice per group). (C, D, E, F) 1D11 rescues acetaldehyde-induced DNA damage in HSCs and Lin– cells. Representative images (C) and quantification (D) of γH2AX foci in HSCs from WT and Fancd2–/– mice are shown. HSCs were pretreated with 1D11 or isotype control antibody followed by exposure to acetaldehyde for 4h, and harvested for immunofluorescence at the indicated time points. Hundred to 200 cells with more than 5 foci were counted for each sample. (E) Representative images of alkaline comets of bone marrow Lineage-negative cells from WT and Fancd2–/– mice. Comet tails of Fancd2–/– cells in the isotype plus acetaldehyde treatment group are highlighted by a star. (F) Olive tail moment demonstrating that 1D11 significantly prevents acetaldehyde-induced DNA damage in Fancd2–/– bone marrow in vitro. Ninety-eight to 275 cells from each group were scored. Error bars represent s.e.m. See also FIG. 6.

FIG. 5. TGF-β Pathway Inhibition Upregulates HR and Downregulates NHEJ in HSCs from Fancd2–/– mice. FA (A) TGF-β pathway inhibition induces expression of the majority genes involved in DNA damage repair in HSCs from WT mice. HSCs were sorted from WT mice after 48h treatment with 1D11 or isotype control antibody, and used for qRT-PCR analysis. (B) The expression levels of DNA damage repair genes in Fancd2–/– and WT HSCs. Some genes involved in HR and NHEJ pathways were pointed out by arrow. (C) Blockade of TGF-β pathway induces HR gene expression and downregulates NHEJ gene expression in HSCs from Fancd2–/– mice. HSCs were sorted from Fancd2–/– mice after 48h treatment with 1D11 or isotype control antibody, and used for qRT-PCR analysis. Some genes involved in HR and NHEJ pathways were pointed out by arrow. (D, E) Gene expression of representative NHEJ (D) and HR (E) genes Lig4, Prkdc, Brca2, and Xrcc1 in HSCs. (F) The frequency of HSCs in Fancd2–/– mice after 48h treatment with 1D11 or isotype control antibody (n=4 mice per group). (G) Schematic of acetaldehyde sensitivity assay in bone marrow HSPCs from WT or Fancd2–/– mice. (H) 1D11 does not protect the Fancd2–/– HSPCs from genotoxic stress when HR is inhibited. HSPCs from WT or Fancd2–/– mice were exposed to 1D11 and RAD51 inhibitors (10 μM) for 30 min followed by exposure to acetaldehyde for 4 hrs. The cells were then washed and cultured in presence of 1D11 and RAD51 inhibitors for five days and survival was determined. Error bars represent mean±s.e.m. *p<0.05; **p<0.01. See also FIG. 8.

FIG. 6. Inhibition of TGF-β Pathway Rescues Acetaldehyde-induced Genotoxicity in HSPCs from FA Mice.

(A) Acetaldehyde sensitivity of Lin– cells from bone marrow of WT or Fancd2–/– mice incubated with isotype control or 1D11 antibody (10 μg/mL). Cells were exposed to 2-8 mM acetaldehyde for 4 hours and survival was determined by counting live cell numbers after 4 days in culture. Error bars represent mean±s.e.m. (B) Representative FACS plots of the peripheral blood samples after staining with antibodies against CD45.1 or CD45.2 are shown. Lin– cells from WT or Fancd2–/– murine bone marrow were exposed to acetaldehyde for 3 hrs and then cultured with isotype or 1D11 antibody before transplantation into lethally irradiated recipients. The peripheral blood from recipients was analyzed for donor cell engraftment at 4 weeks after transplantation by staining with CD45.1 and CD45.2 antibodies. The percentage of donor-derived CD45.2+ cells or recipient-derived CD45.1+ cells in peripheral blood of recipients are shown in FACS plots. The average percentage of CD45.2+ cells are shown in the plot. (C) Lineage distribution of donor-derived cells (CD45.2) in peripheral blood of recipients as detected after staining the blood samples with antibodies against lineage markers in the transplantation experiments described in (B). (n=5 mice per group). Error bars represent mean±s.e.m. (D) DNA repair kinetics in WT and Fancd2−/− Lin− immature cells as shown by the percentage of cells with γH2AX foci. Lin− cells were exposed to 4 mM acetaldehyde for 4 hrs and allowed to recover in presence of isotype or 1D11 antibody. The cells were analyzed for γH2AX foci and 30-100 cells were counted in each time point. (E) Schematic of acetaldehyde and 1D11/isotype antibody treatments in vitro. Lineage-negative cells from bone marrow of WT and Fancd2−/− mice were pretreated with 1D11 or isotype for 30 min followed by 4h treatment with 4 mM acetaldehyde. After washing out, the cells were allowed to recover for 4h in presence of 1D11 or isotype antibody. DNA damage was assessed by a single cell comet tail assay.

FIG. 7. Inhibition of TGF-β Pathway Promotes DNA Repair in HSPCs from pI:pC-treated FA Mice.

(A) Physiological stress induced by pI:pC activates TGF-β pathway in HSPCs. Phospho-Smad2/3 levels in HSPCs of pI:pC- or TGFβ1-treated mice were analyzed by flow cytometry. (B) Representative immunofluorescence staining showing γH2AX and 53BP1 foci in HSCs from WT and Fancd2−/− mice treated with pI:pC (5 mg/kg) plus 1D11 or isotype antibody (10 mg/kg) for 48h. (C) Representative images of alkaline comets of HSCs from WT and Fancd2−/− mice are shown. (D) Total BM cell numbers in WT and Fancd2−/− mice treated with pI:pC plus 1D11 or isotype antibody. (E) DCF-DA staining showing that inhibition of TGF-β pathway does not reduce pI:pC-induced reactive oxygen species (ROS) levels in Fancd2−/− HSPCs. Mice were treated with pI:pC plus 1D11 or isotype antibody and after 48 hrs, HSPCs were analyzed. (F) Inhibition of TGF-β pathway partially prevents pI:pC-induced exit from quiescence of HSCs. (n=3 mice per group). (G) Representative immunofluorescence staining showing γH2AX foci in HSPCs from WT and Fancd2−/− mice treated with pI:pC plus 1D11 for four weeks.

FIG. 8. Inhibition of TGF-β Pathway in murine HSPCs Promotes DNA Repair Activity.

(A) Experimental scheme for inhibition of TGF-β Pathway in mice. WT or Fancd2−/− mice were treated with isotype or 1D11 antibody (10 mg/kg) for 48h, and bone marrow HSCs were sorted for gene expression profile and cell cycle analysis. (B) Increased number of Fancd2−/− HSCs in S-G2M phase of cell cycle after 1D11 treatment. Cell cycle analysis of HSCs from WT or Fancd2−/− mice treated with isotype or 1D11 antibody for 48h is shown. Error bars represent mean±s.e.m. (n=4 mice per group). (C) Representative immunoblots showing 1D11 efficiently inhibits the level of p-Smad2 in hematopoietic progenitors from Fancd2−/− mice. (D) RAD51 inhibitors, RI-1 and B02, significantly decrease HR efficiency. Homologous recombination assay was measured in U2OS cells with DR-GFP reporter after treatment with 1004 RI-1 and 10 μM B02. The representative of two independent experiments is presented; error bars represent mean±s.e.m. (E, F) RAD51 inhibitors, RI-1 and B02, efficiently block RAD51 foci formation. GM6914 (FA-A) cells or corrected GM6914+FANCA cells were treated with 1 μM MMC and 10 μM inhibitors for 6h before immunofluorescence analysis. Representative images (E) and quantification (F) of RAD51 foci are shown. (G) RAD51 inhibitors do not show cytotoxicity in HSPCs. HSPCs from WT or Fancd2−/− mice were treated with B02 (10 μM) or RI-1 (1004) in vitro for five days and survival was determined. (H) Colony forming assay showed that RAD51 inhibitors block the protective function of 1D11 after genotoxic stress in Fancd2−/− HSPCs. HSPCs from WT or Fancd2−/− mice were exposed to 1D11 (10 μg/mL) and RAD51 inhibitors (10 μM) for 30 min followed by exposure to acetaldehyde for 4 hrs. The cells were then washed and cultured in presence of 1D11 and RAD51 inhibitors for 7-9 days, and hematopoietic colonies were counted.

DETAILED DESCRIPTION OF THE INVENTION

The invention is based in part upon the surprising discovery that inhibition of the TGF β signaling pathway will rescue the growth of bone marrow cells in patients with Fanconi Anemia (FA).

More specifically, it was discovered that blocking the transforming growth factor β (TGFβ) pathway, by either genetic deletion or pharmacologic inhibition, significantly enhanced FA cellular growth and improved cellular survival in the presence of DNA interstrand crosslinking agents.

Blocking the TGF-β pathway improves the survival of FA cells and rescues the proliferative and functional defects of HSPCs derived from FA mice and FA patients. Inhibition of TGF-β signaling in FA HSPCs results in elevated homologous recombination (HR) repair with a concomitant decrease in non-homologous end-joining (NHEJ), accounting for the improvement in cellular growth.

In humans, three isoforms of TGFβ, TGFβ1, TGFβ2 and TGFβ3, are known to exist. (Swiss Prot accession numbers P001137, P08112 and P10600 (respectively)). In their biologically active state, these three isoforms are 25 kDa homodimers comprising two 112 amino acid monomers joined by an inter-chain disulfide bridge. TGFβ1 differs from TGFβ2 by 27 amino acids, and from TGFβ3 by 22 amino acids. The differences are mainly conservative amino acid changes. The three-dimensional structure of TGFβ has been determined by X-ray crystallography and the receptor binding regions have been defined. Both human TGFβs and mouse TGFβs are similar. The human TGFβ1 has one amino acid difference from a mouse TGFβ1. Human TGFβ2 has only a three amino acid difference from mouse TGFβ2, and human and mice TGFβ3 are identical. One neutralizing mouse monoclonal antibody that binds TGFβ1, TGFβ2 and TGFβ3 isoforms is known as 1D11 and is available from R&D Systems (Catalog No. MAB-1835) through the ATCC (Accession No. HB 9849). Fresolimumab, also known as GC1008, (CAS Registry Number: 948564-73-6) is a humanized monoclonal IgG4 antibody that neutralizes all TGFβ isoforms and is suitable for therapeutic use in humans.

Bone marrow stromal cells derived from Fancd2-deficient mouse exhibited hyperactive noncanonical TGFβ-Erk pathway, and inhibition of this pathway also restored resistance to genotoxic agents. Moreover, inhibition of the canonical TGFβ-Smad pathway rescued the proliferation defect of hematopoietic stem/progenitor cells (HSPCs) from Fancd2-deficient mice and human FA patients. Mechanistically, hyperactive TGFβ signaling in FA cells resulted in elevated non-homologous end joining (NHEJ) activity and reduced homologous recombination (HR) repair. The activation of HR repair by TGFβ inhibition accounts, at least in part, for the improvement in cellular growth. Taken together, inhibition of the TGFβ signaling pathway will provide a therapeutic strategy in the clinical treatment of FA patients with bone marrow failure.

Despite the elucidation of the FA/BRCA pathway[2,3], the pathophysiological mechanism of BMF in FA has remained elusive. Research has been hampered by the fact that FA pathway-deficient mice do not spontaneously develop bone marrow failure[12]. Recent studies have demonstrated that HSPCs from FA patients and FA mice have a hyperactive p53/p21 axis, resulting, at least in part, in the increased BMF[9]. The hyperactivation of p53/p21 appears to result from unresolved DNA replication stress, endogenous DNA damage, and other cellular stresses. The progressive impairment of HSPC by p53-mediated cell cycle arrest and apoptosis also accounts for the observed delay in onset of BMF in FA patients.

Here, we describe a novel mechanism for BMF in FA patients and mouse models—namely, the hyperactivation of the TGFβ pathway in FA HSPCs and stromal bone marrow fibroblasts. Using an unbiased shRNA screen, we initially identified hyperactive components of the TGFβ signaling pathway, which suppress the growth of FA patient-derived cell lines. Inhibition of TGFβ pathway, in HSPCs and in primary bone marrow stromal cells, partially rescued the growth and crosslinker hypersensitivity of these cells. Bone marrow failure is treated, prevented or delayed, by administering to a subject having Fanconi Anemia a composition comprising fresolimumab, 1D11 or an antigen binding fragment thereof. In other aspects, fresolimumab, 1D11 or an antigen binding fragment threod is administered to a subject that is to receive a bone marrow transplant.

Treatment is efficacious if the treatment leads to clinical benefit such as, an increase in bone marrow stems cells and/or bone marrow stromal fibroblast cells in the patient. When treatment is applied prophylactically, "efficacious" means that the treatment retards or prevents bone marrow failure or alleviates a clinical symptom of bone marrow failure such as decreasing blood count. Efficaciousness is determined in association with any known method for diagnosing or treating bone marrow failure.

Fresolimumab, 1D11 or an antigen binding fragment thereof is administered before the patient is prepared for a bone marrow transplant, after a bone marrow transplant or both. Alternatively, fresolimumab, 1D11 or an antigen binding fragment thereof is administered after the patient is prepared for a bone marrow transplant but before the bone marrow transplant. By prepared for a bone marrow transplant is meant that the paint has had undergone a conditioning regimen such a chemotherapy, total body irradiation, or both to weaken or destroy the unhealthy bone marrow.

In other embodiments, fresolimumab, 1D11 or an antigen binding fragment thereof is administered to subject during a medical crisis such as a bacterial or viral infection.

Therapeutic Administration

The invention includes administering to a subject having Fanconi Anemia a composition comprising a fresolimumab (GC1008), 1D11 or an antigen binding fragment thereof.

An effective amount of a therapeutic compound is preferably from about 0.1 mg/kg to about 150 mg/kg. More preferably, 0.5 mg/kg to 10 mg/kg, even more preferably 1 mg/kg to 5 mg/kg. Effective doses vary, as recognized by those skilled in the art, depending on route of administration, excipient usage, and coadministration with other therapeutic treatments including use of other therapeutic agents for treating, preventing or alleviating bone marrow failure such as androgen therapy or erythropoietin.

A therapeutic regimen is carried out by identifying a mammal, e.g., a human patient suffering from Fanconi Anemia by standard methods.

Doses may be administered once, or more than once. In some embodiments, it is preferred that the therapeutic compound is administered once a week, twice a week, three times a week, four times a week, five times a week, six times a week, or seven times a week for a predetermined duration of time, most preferably 3 times per week although less frequent dosing may be preferred if targeting the blood compartment as in Fanconia Anemia. The predetermined duration of time may be 1 week, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, or up to 1 year, preferably for 1 to two months. In some cases, chronic administration may be desired, especially in the treatment of a condition lasting more than three months like Fanconia Anemia. The terms "chronic administration" or "administered chronically" mean prolonged drug administration for a duration of greater than three months.

The pharmaceutical compound is administered to such an individual using methods known in the art. Preferably, the compound is administered orally, rectally, nasally, topically or parenterally, e.g., subcutaneously, intraperitoneally, intramuscularly, and intravenously, preferably intravenously. The inhibitors are optionally formulated as a component of a cocktail of therapeutic drugs. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds are administered by implanting (either directly into an organ or subcutaneously) a solid or resorbable matrix which slowly releases the compound into adjacent and surrounding tissues of the subject.

Definitions

The term "TGFβ" or "transforming growth factor-beta" refers to the family of molecules described that have either the full-length, native amino acid sequence of any of the humans TGFβ isoforms.

A "TGFβ antibody" or antigen binding fragment thereof refers to an antibody that binds to any of the isoforms of TGFβ, preferably binding to either TGFβ1, TGFβ2, or TGFβ3, or to any combination thereof.

The term "polypeptide" refers, in one embodiment, to a protein or, in another embodiment, to protein fragment or fragments or, in another embodiment, a string of amino acids. In one embodiment, reference to "peptide" or "polypeptide" when in reference to any polypeptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The term "homology", when in reference to any nucleic acid sequence indicates a percentage of nucleotides in a candidate sequence that are identical with the nucleotides of a corresponding native nucleic acid sequence. Homology may be determined by computer algorithm for sequence alignment, by methods well described in the art. For example, computer algorithm analysis of nucleic acid or amino acid sequence homology may include the utilization of any number of software packages available, such as, for example, the BLAST, DOMAIN, BEAUTY (BLAST Enhanced Alignment Utility), GENPEPT and TREMBL packages.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological crossreactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, delaying the onset of or a combination thereof. Treating refers inter alia to increasing time to sustained progression, expediting remission, inducing remission, augmenting remission, speeding recovery, increasing efficacy of or decreasing resistance to alternative therapeutics, or a combination thereof "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The terms "patient" "subject" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

EXAMPLES

Example 1: General Methods

Animals

We generated Fancd2$^{-/-}$ mice as previously described[12]. C57BL/6J-CD45.1, and C57BL/6J-CD45.2 mice were obtained from mice were purchased from The Jackson Laboratory. All mice were in C57BL/6J background, and were bred and maintained in a temperature- and humidity-controlled environment and given unrestricted access to 6% chow diet and acidified water. We treated WT and Fancd2$^{-/-}$ mice with 0.3 mg/kg MMC to induce bone marrow failure. The neutralizing anti-mouse TGFβ monoclonal antibody 1D11 was provided by Genzyme, and administrated mice at 10 mg/kg by intraperitoneal injections three time per week. Animal experiments were performed following the approved protocol of the Animal Care and Use Committee at the Dana Farber Cancer Institute.

Hematopoietic Stem/Progenitor Cell Culture and Flow Cytometry Analysis.

For mouse hematopoietic stem/progenitor cell culture, Lin$^-$ cells were cultured in vitro in StemSpan SFEM media with 10 ng/mL SCF, 20 ng/mL IGF-2, 20 ng/mL TPO, 10 ng/mL heparin, and 10 ng/mL a-FGF. Half media was changed every three days. For human cord blood cells, CD34+ cells were isolated using CD34 microbead kit (Miltenyi Biotec). Cells were cultured in StemSpan SFEM media with 100 ng/mL hSCF, 100 ng/mL FLT3 ligand, 10 ng/mL TPO, 10 ng/mL IL-6. Cells were treated with 10 ug/mL 1D11 or 10 μM SD208.

To perform flow cytometry analysis, Lin$^-$ cells were collected at day 2 and 5 post transduction and suspended in staining medium (PBS with 2% heat-inactivated calf serum), and incubated with PE-conjugated c-Kit and APC-conjugated Sca-1 antibodies were added to the cells for 30 min at 4° C. in the dark. Stem cell population (GFP$^+$Lin$^-$c-Kit$^+$Sca-1$^+$) was analyzed by FACS. All these antibodies were purchased from eBioscience.

Functional Cell-Based Assays

For survival assays, cells were seeded at a density of $1\times10^3$ cells per well in 96-well plates. After 72 hours of culture in indicated concentrations of MMC or post exposure of acetaldehyde, viability was assessed using CellTiterGlo reagent (Promega). In order to assess clonogenicity, cells were seeded at a low density (500-1000 cells per well) in 6-well plates and allowed to form colonies. The cells were then fixed in methanol/20% acetic acid and stained with 1% crystal violet. Colony formation was assessed by solubilizing crystal violet stain with methanol and quantifying UV absorbance for each condition.

ELISA

Cell culture supernatant were harvested, and the TGFβ1 level was assessed using TGF-β1 Multispecies ELISA Kit (Invitrogen) following the manual procedure.

Immunofluorescence

Cells were grown on coverslip for 24 hours before treated with MMC. Cells were fixed with 4% (w/v) paraformaldehyde for 10 min at room temperature, washed three times with PBS, followed by extraction with 0.3% Triton X-10 for 10 min on ice. The incubation with the primary antibody (anti-RAD51, Santa Cruz) was done at 37° C.

Comet Assay

To evaluate MMC induced DNA cross-link damage and repair, a modified alkaline Comet assay was performed[37,38]. Briefly, cells were seeded into 6-well plates at 20% confluence and treated with MMC for 6 hours, and washed and release for 24 and 48 hours. Cells were collected, placed on slide coated with agarose, and lysed according to manufacturer's protocol of Trevigen's Comet Assay Kit (Trevigen). After lysis, the slides were irradiated to induce strand breaks with 5 Gy γ-radiation. Electrophoresis was conducted, and comets were visualized using an Axio Imager Z1 fluorescence microscope with an AxioCam MRm CCD camera (Zeiss, Thornwood, N.Y.).

Real Time RT-PCR

Total RNA was isolated using the RNeasy Mini kit (Qiagen, CA). cDNA was synthesized using High-Capacity cDNA Reverse Transcription Kit (Life Technologies). All real time PCR reactions were done using Vii A 7 PCR machine. 204 reaction system was composed of 104 SYBR Green, 2.5 μM 20 uM primer mixture, 10 ng cDNA and nuclease-free water. All experiments were performed in triplicate. Gapdh was the internal control. The primer sequences were shown as follows: Tgfb1 sense: CAGCTC-CTCATCGTGTTGGTG (SEQ ID NO: 1); Tgfb1 antisense: GCACATACAAATGGCCTGTCTC (SEQ ID NO: 2); Smad3 sense: CACGCAGAACGTGAACACC (SEQ ID NO: 3); Smad3 antisense: GGCAGTAGATAACGT-GAGGGA (SEQ ID NO: 4); Gapdh sense: TGGATTTG-GACGCATTGGTC (SEQ ID NO: 5); Gapdh antisense: TTTGCACTGGTACGTGTTGAT (SEQ ID NO: 6).

Murine Bone Marrow Transplantation

Donor cells (CD45.2$^+$ were transplanted into lethally irradiated (10 Gy dose) recipient (congenic B6-CD45.1$^+$ mice) along with 1×10$^5$ cells competitive bone marrow cells from congenic B6-CD45.1$^+$ mice. Peripheral blood from recipient mice was analyzed for donor cell engraftment as described (Parmar et al., 2010).

Colony-Forming Unit-Spleen (CFU-S) Assay

Recipient mice (wild-type, 8-12 weeks old) were irradiated with a split dose of 1100 rad (550 rad each, 4 hours apart) before transplantation. Forty thousand bone marrow cells from donor mice were transplanted into each recipient mouse. Ten to 12 days post-transplantation, spleens were harvested and fixed with Bouin fixative solution.

In Vivo Xenograft Assay

Human cord blood derived CD34$^+$ cells were transduced with lentivirus encoding shFANCD2 or shControl as described (Ceccaldi et al., 2012). While cells were selected with 2 μg/mL puromycin, cells were also treated with 10 μg/mL GC1008. After 48h treatment, 2×10$^5$ cells were transplanted into sub-lethally irradiated (2.5 Gy) NSG mice. The recipient mice were treated with 10 mg/kg GC1008 at 3 doses per week for two weeks. Two and eight weeks after transplantation, human cells in peripheral blood (PB) were analyzed using anti-human CD45 antibody (eBioscience, 17-0459-42) by flow cytometry.

TGF-β Pathway Activity Using Luciferase Reporter Assay 293T cells were transiently transfected with a TGF-β responsive luciferase promoter (CAGA-luc) plasmid (kindly provided by H. Y. Lin, Massachusetts General Hospital) along with FANCD2 or control vector. Cells were harvested at 48h after transfection and luciferase activity was determined using the Dual-Lucifease Reporter Assay system (Promega).

Traffic Light Reporter (TLR) Assay

Genome engineering experiments were performed as previously described (Certo et al., 2011). Briefly, single copy of TLR cell lines including FANCA-/- fibroblast cells (GM6914) and FANCA corrected GM6914 with or without shSMAD3 were generated by transducing cells with TLR-BFP reporter lentivirus, typically yielding ~5% transduction based on fluorescence. Two days after transduction, transduced cells (BFP+) were sorted by FACS. To generate double strand break, cells were seeded at 2×105 cells per well in 6-well plate 24h before transduction, and cells were transduced with lentivirus containing I-SceI alone or I-SceI plus GFP donor template. For SD208 treatment, cells were treated with 10 μM SD208 after 3-4h post-transduction. All transductions were carried out in the presence of 8 μg/mL polybrene. Twenty-four hours after transduction, medium was changed. Genome engineering events were analyzed by flow cytometry at 72 hours after transduction. NHEJ is represented bymCherry fluorescence, and HR by GFP fluorescence.

Drug Sensitivity Assays

For survival assays, cells were seeded at a density of 1×103 cells per well in 96-well plates. After 3-6 days of culture in indicated concentrations of MMC or post exposure of acetaldehyde, viability was assessed using CellTiterGlo reagent (Promega). In order to assess clonogenicity, cells were seeded at a low density (500-1000 cells per well) in 6-well plates and allowed to form colonies. The cells were then fixed in methanol/20% acetic acid and stained with 1% crystal violet. Colonies were counted after crystal violet staining.

Chromatin Immunoprecipitation (ChIP) Assay

The ChIP assay was performed as described previously (Park et al., 2013). Briefly, 10×106 cells were treated with MMC (1 μM) for 8 hours. Cells were chemically crosslinked with 1% formaldehyde for 15 min at room temperature. Cells were rinsed twice with 1×PBS and harvested in Farnham lysis buffer (5 mM PIPES pH8.0, 85 mM KCl, 0.5% NP-40, and protease inhibitor cocktail). After washing, cells were resuspended in sonication buffer (PBS, 1% NP-40, 0.5% sodium deoxycholate, 0.1% SDS, and protease inhibitor cocktail), and sonicated with 10×30 seconds pulses, 5 min in total, 18-21 Watts of power. After sonication, 5% samples were used as input. Sonicated samples were further divided in half, and incubated overnight with 100 μL of Dynal Protein G magnetic beads that had been preincubated with anti-FANCD2 (Novus Biologicals, NB100-316) or IgG control antibody. Beads were washed 5× with LiCl wash buffer (100 mM Tris pH 7.5, 500 mM LiCl, 1% NP-40, 1% sodium deoxycholate), and 1×TE buffer containing 50 mM NaCl. Bound complexes were eluted from the beads by heating at 65° C. for 1 hour (vortexing every 5 min). Crosslinking was reversed by incubating samples at 65° C. for overnight. DNA was purified and then analyzed by real-time PCR using SMAD1 promoter primers (primer #1: 5' AAGGCAGGAGAATTGCTTGA-3' (SEQ ID NO: 7), 5'-CCTTCACCTTCTGCCATGAT-3' (SEQ ID NO: 8); primer#2: 5'-CAAGGGAGGGTTTCAACAG-3' (SEQ ID NO: 9), 5'-TGAGCACTTACTGGTCAATTCG-3' (SEQ ID NO: 10)).

Figure 2A:
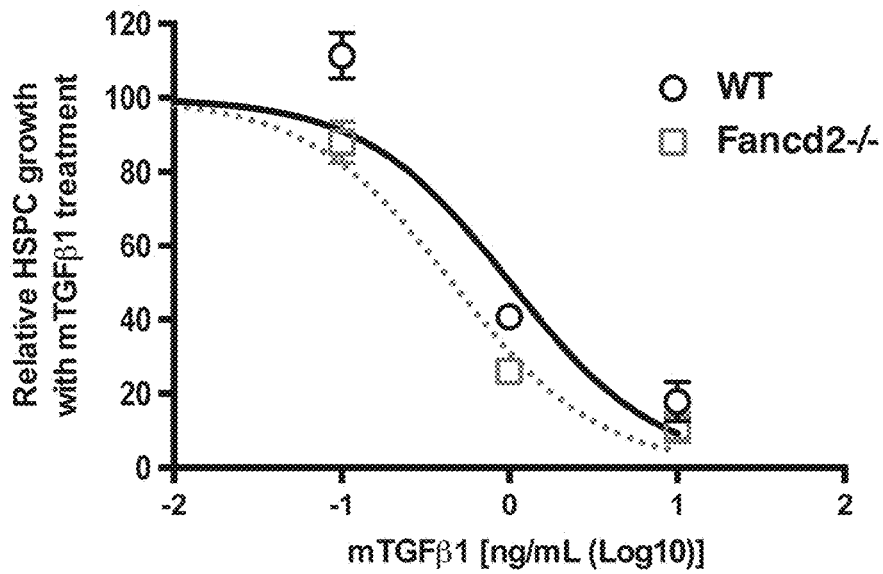
Figure 2B:
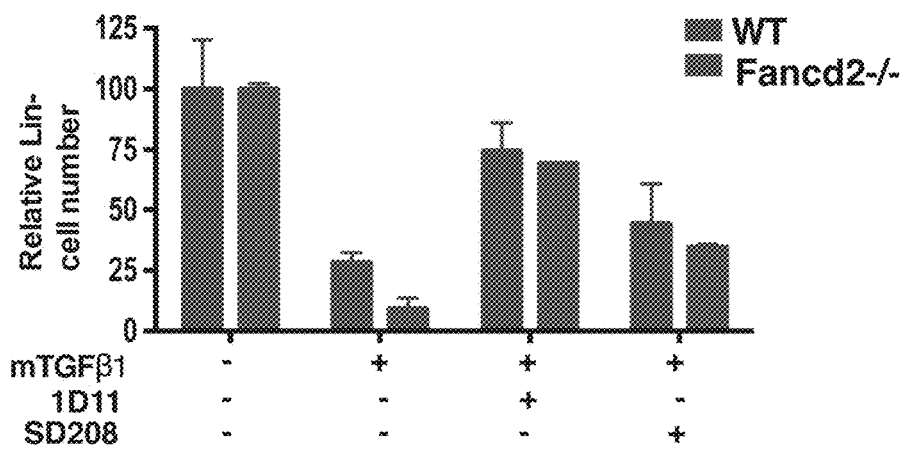
Figure 2C:
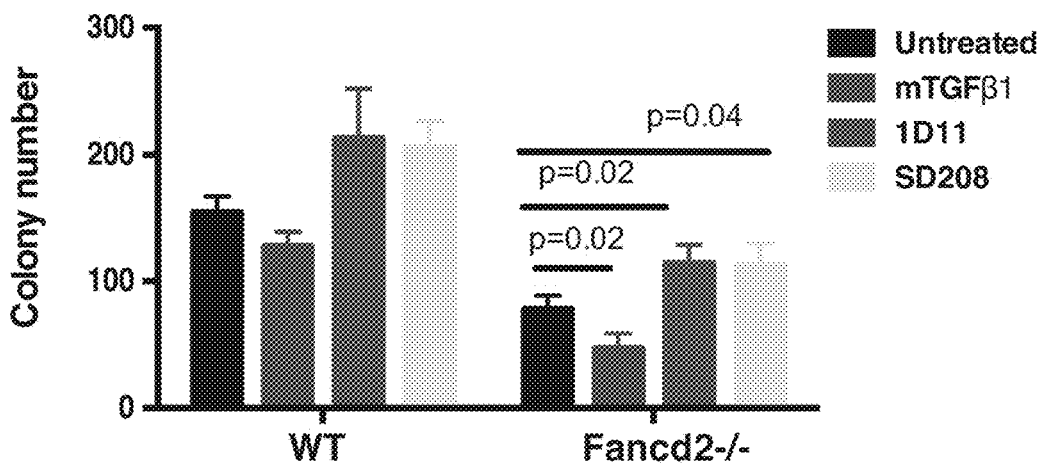

Example 2: TGFβ Pathway Inhibition Corrects Compromised Stem Cell Function of FA Mice Bone marrow failure in FA results from impaired stem cell function caused by endogenous genotoxins[2,28,32]. Additionally, compared to WT HSPCs, Fancd2−/− HSPCs are hypersensitive to TGFβ (FIG. 2A). Therefore, we hypothesized that inhibition of TGFβ pathway may correct the defective function of stem cells collected from FA mice. To block the TGFβ pathway, we use the anti-murine TGFβ monoclonal antibody 1D11, because it has been shown to promote the regeneration of bone marrow in murine models. Blockage of TGFβ using this neutralizing antibody 1D11 promotes multilineage hematopoietic regeneration in the 5-FU-treated myelosuppression murine model[21]. Treatment with 1D11 antibody significantly blocked the activation of the TGFβ pathway in murine stromal cells, and rescued MMC sensitivity of Fancd2$^{-/-}$ stromal cells (FIG. 1A). Importantly, 1D11 treatment also corrected the suppressive effects caused by either exogeneous TGFβ1 (FIG. 2B) or endogenous TGFβ signaling (FIG. 2C). These data demonstrate that 1D11 can efficiently block the TGFβ pathway.

Figure 1B:
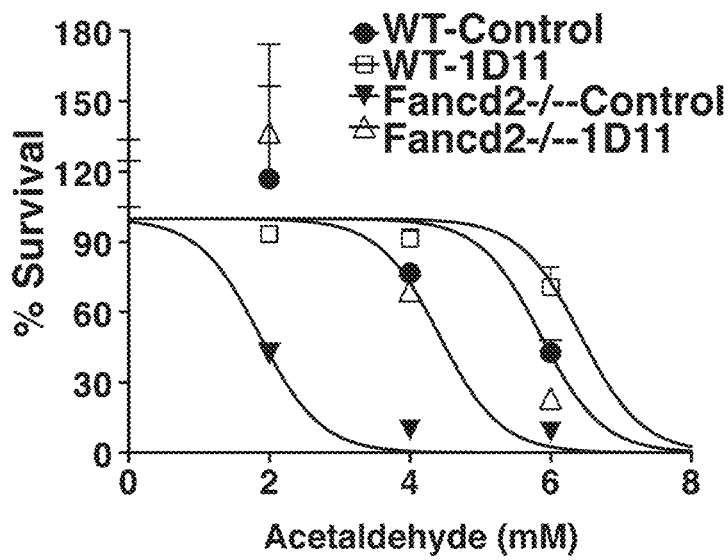
Figure 1C:
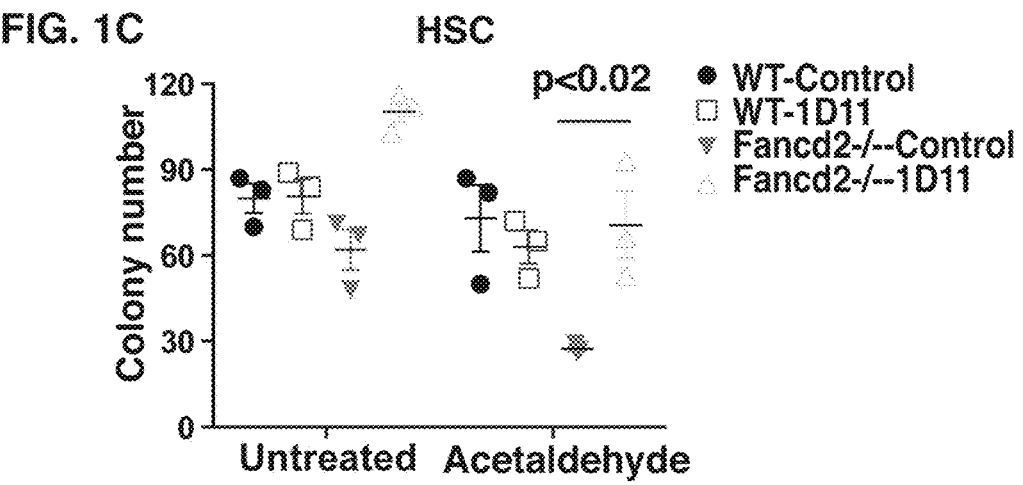
Figure 1D:
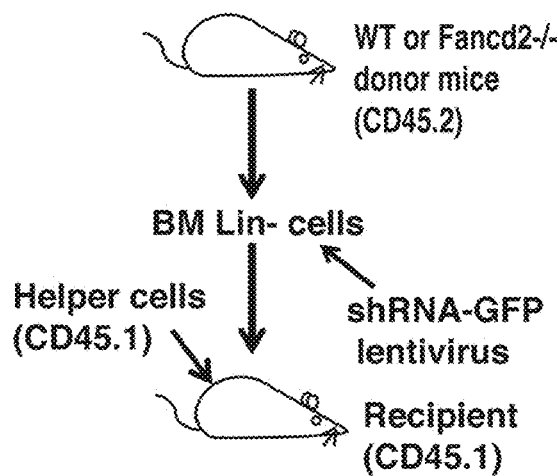
Figure 1E:
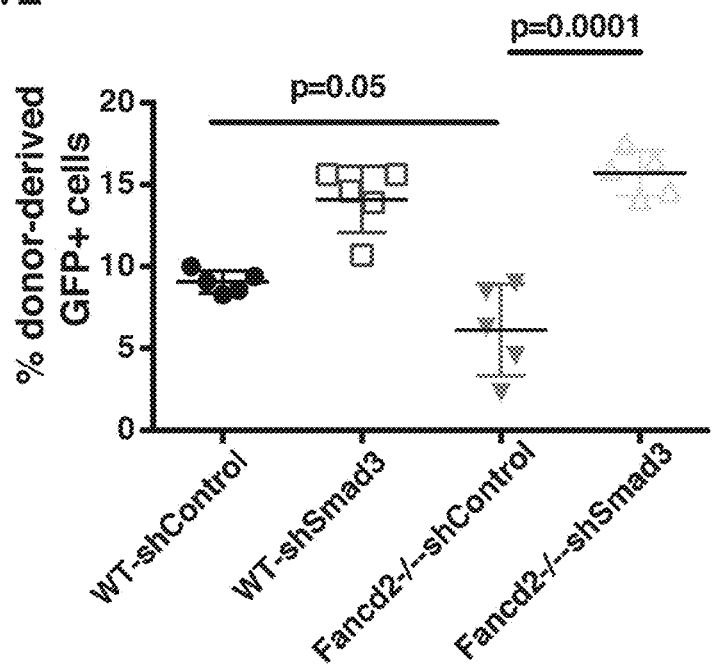
Figure 2D:
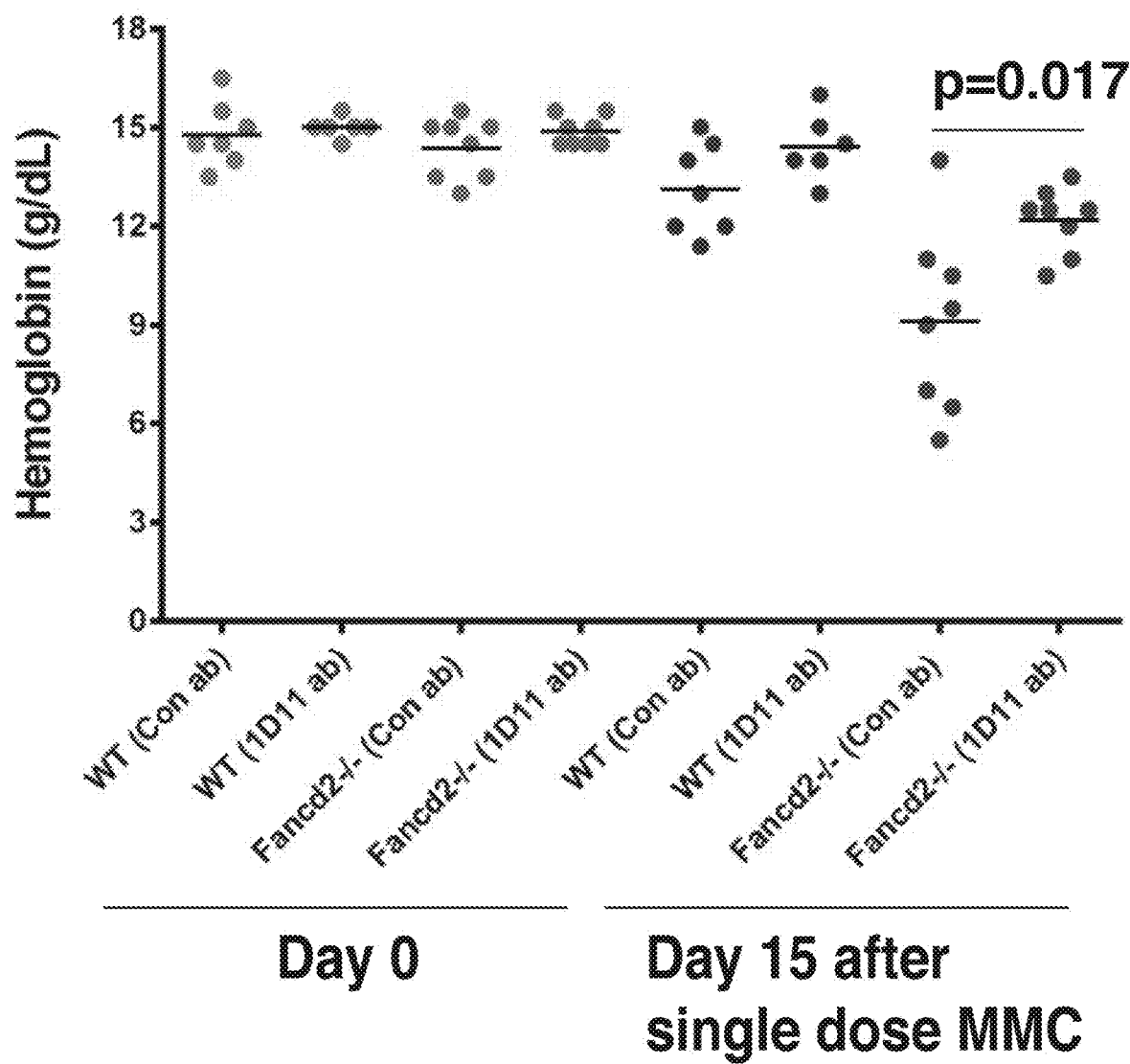
Figure 2E:
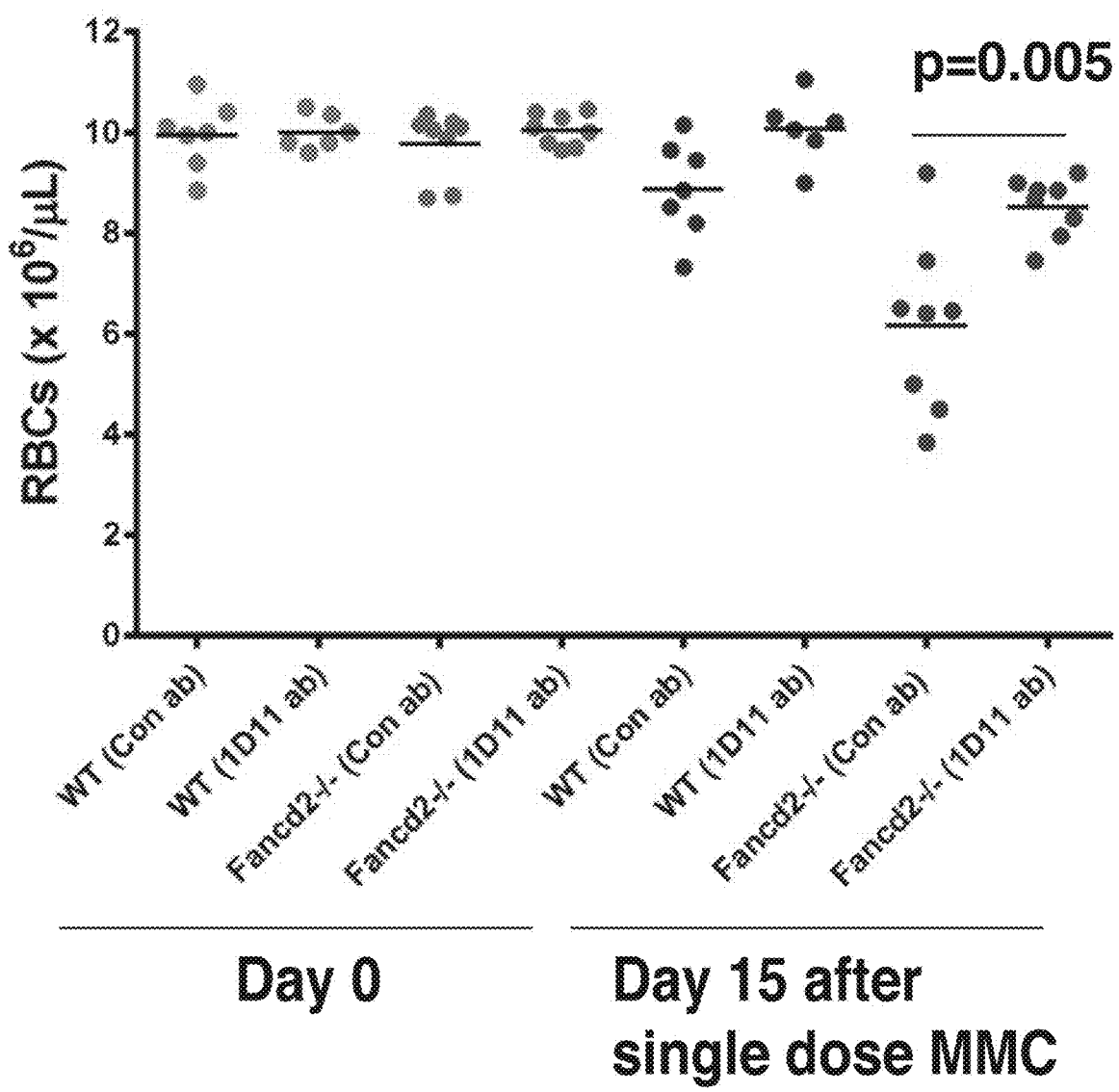

Next, we investigated the potential effect of 1D11 on Fancd2$^{-/-}$ HSPCs in the presence of acetaldehyde. As expected, both Lin$^-$ cells and HSCs from Fancd2$^{-/-}$ mice were more sensitive to acetaldehyde than congenic controls; in contrast, 1D11 treatment counteracted the genotoxic effects of acetaldehyde, and significantly rescued the growth and clonogenic capacity of Fancd2$^{-/-}$ HSPCs (FIGS. 1B and C). We further examined whether TGFβ pathway inhibition could rescue bone marrow failure in vivo using an MMC-induced bone marrow failure model in FA mice. 1D11 treatment significantly rescued hemoglobin levels and red blood cell counts in Fancd2−/− mice treated with MMC (FIGS. 2D and E). To further assess the effect of TGFβ pathway inhibition on FA HSCs in vivo, we performed an engraftment assay, using control or shSmad3 lentivirus-transduced Lin$^-$cells from WT and Fancd2$^{-/-}$ mice (FIG. 1D). Smad3-deleted Fancd2$^{-/-}$ cells engrafted more efficiently than control cells (FIG. 1E). Taken together, our data indicate that inhibition of the TGFβ pathway by 1D11 restores resistance of HSCs from FA mice to endogenous genotoxins, and partially corrects impaired stem cell function.

Figure 6A:
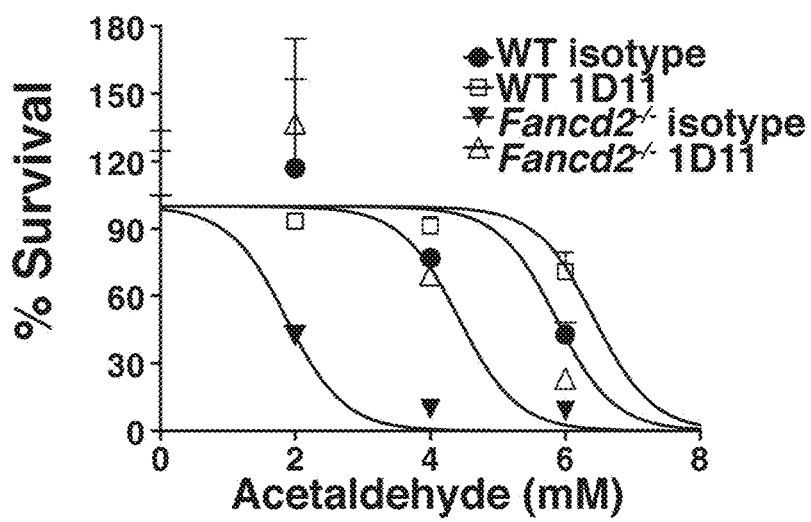
Figure 6B:
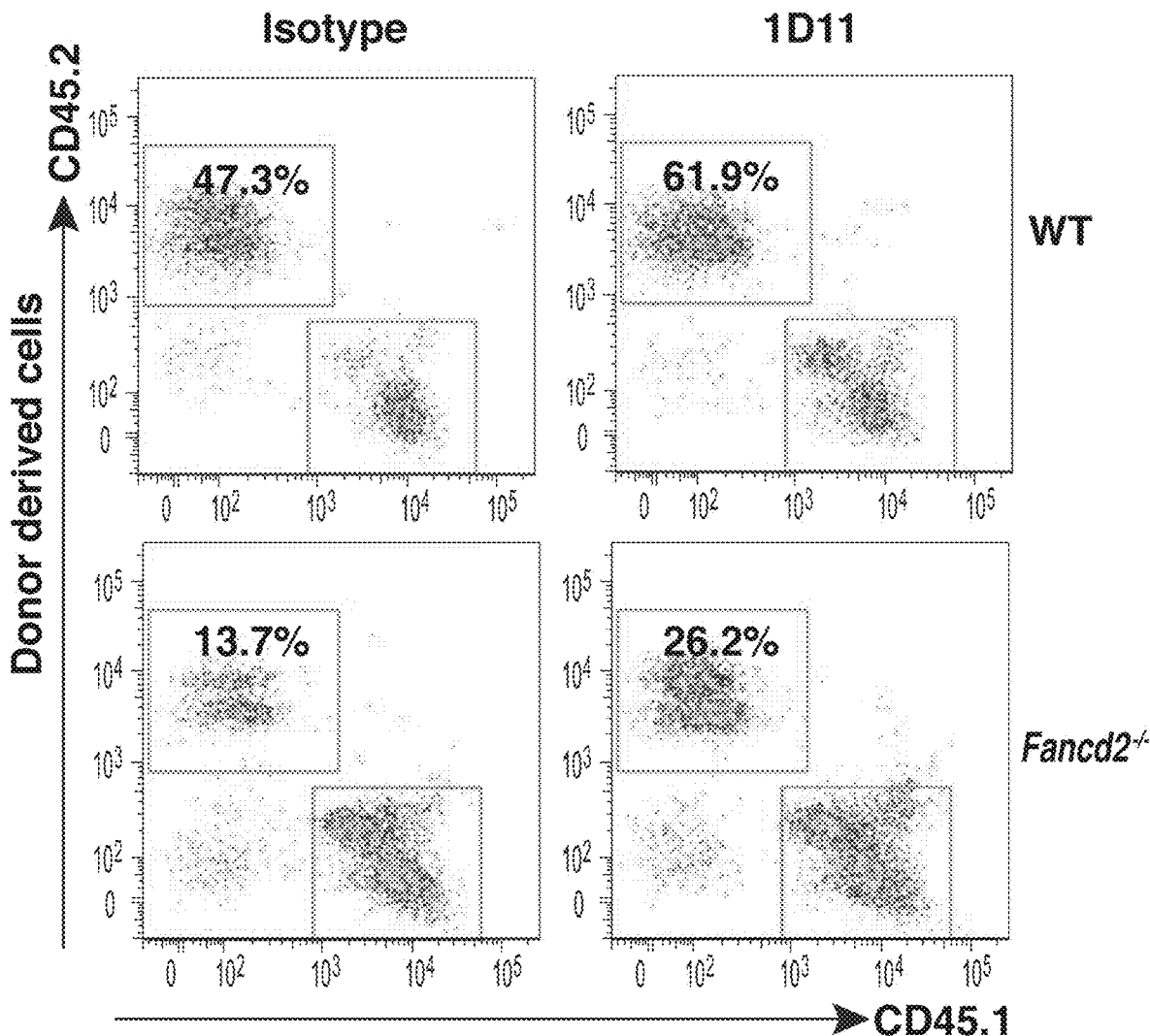
Figure 6C:
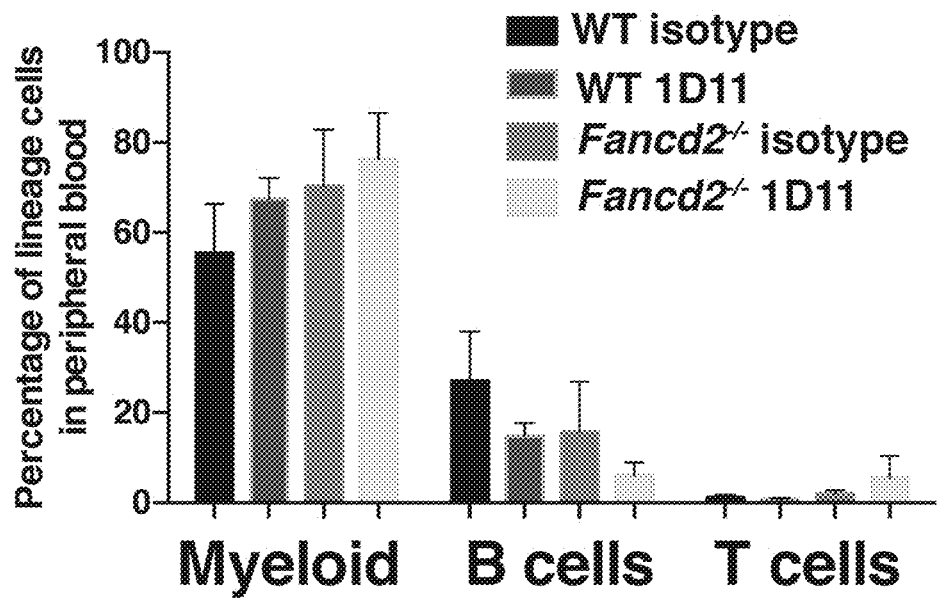
Figure 6D:
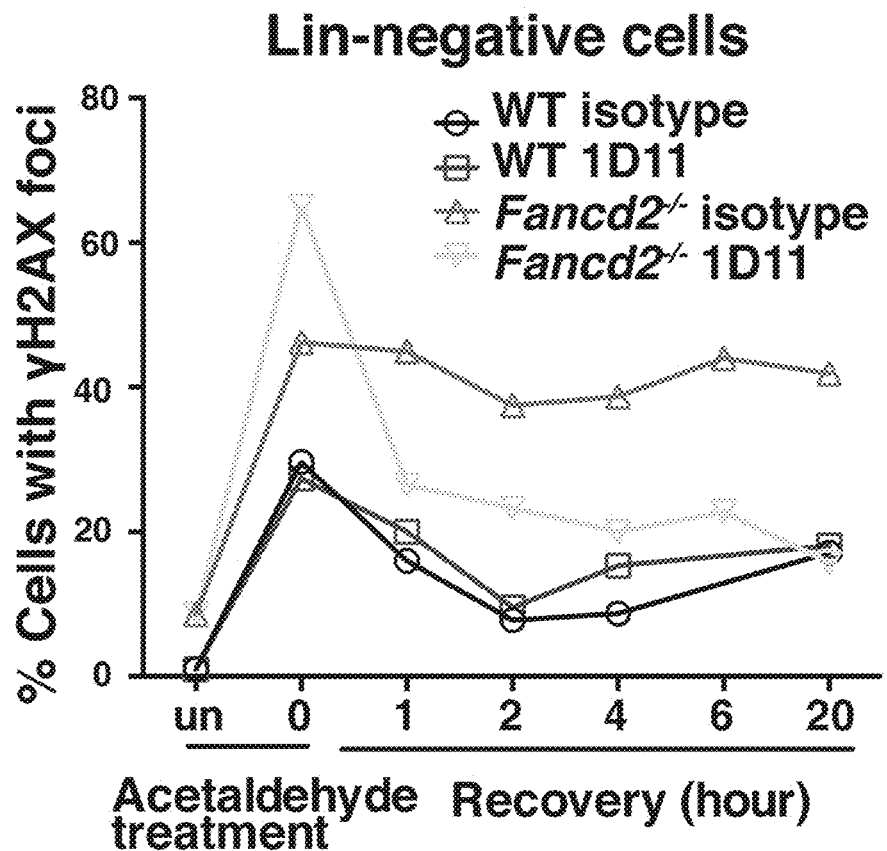
Figure 6E:
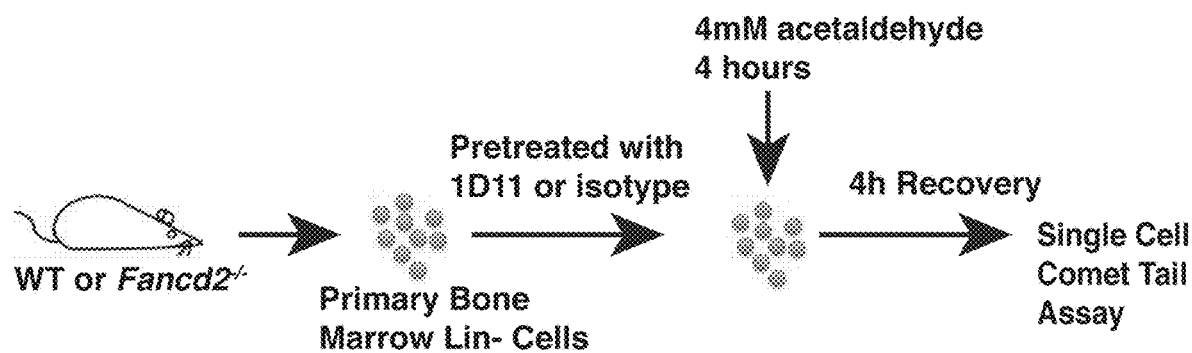

Example 3: TGF-Β Pathway Inhibition Rescues Acetaldehyde-Induced Genotoxicity in HSPCs from FA Mice DNA damage induced by the endogenous genotoxic agents, such as acetaldehyde, causes the attrition of HSCs, leading to spontaneous bone marrow failure in murine FA models (Garaycoechea et al., 2012; Langevin et al., 2011). We reasoned that blockade of the TGF-β pathway may contribute to the repair of acetaldehyde-induced DNA damage in FA HSCs. As expected, bone marrow cells from Fancd2$^{-/-}$ mice were sensitive to acetaldehyde exposure. The neutralizing anti-TGF-β antibody 1D11 treatment counteracted the genotoxic effects of acetaldehyde, and rescued the growth and clonogenic capacity of Fancd2$^{-/-}$ HSCs or Lin$^-$cells from bone marrow (FIGS. 4A and 6A). To directly measure the protective effect of 1D11 on the survival of HSPCs after acetaldehyde exposure, a stem cell transplant was performed. The percentage of donor-derived cells at 4 and 16 weeks post transplantation was higher in recipients of 1D11 treated Fancd2$^{-/-}$ group than those in the isotype control group (FIGS. 4B and 6B), and 1D11 did not significantly affect the lineage differentiation of HSPCs (FIG. 6C). Furthermore, γH2AX foci, a marker for DNA damage, resolved more rapidly in 1D11 treated Fancd2$^{-/-}$ cells, suggesting an improvement of DNA repair (FIGS. 4C, 4D, and 6D). Repair of DNA damage was further confirmed by comet assay (FIGS. 4E, 4F, and 6E). 1D11 treated Fancd2$^{-/-}$ cells also showed improvement in DNA repair when DNA damage was directly assessed by alkaline comet assay and confirmed that acetaldehyde-induced γH2AX foci indeed correspond to unrepaired double strand breaks (FIGS. 4E, 4F, and 6E), Taken together, pharmacologic inhibition of the TGF-β pathway by 1D11 promotes resistance of FA cells to endogenous genotoxic agents, and partially corrects the impaired stem cell function by promoting DNA repair.

Figure 7A:
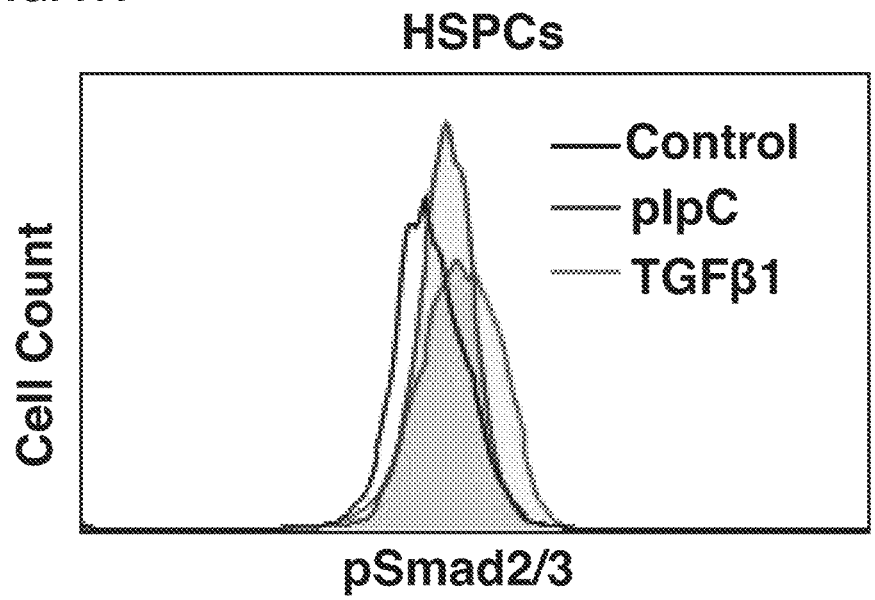
Figure 7B:
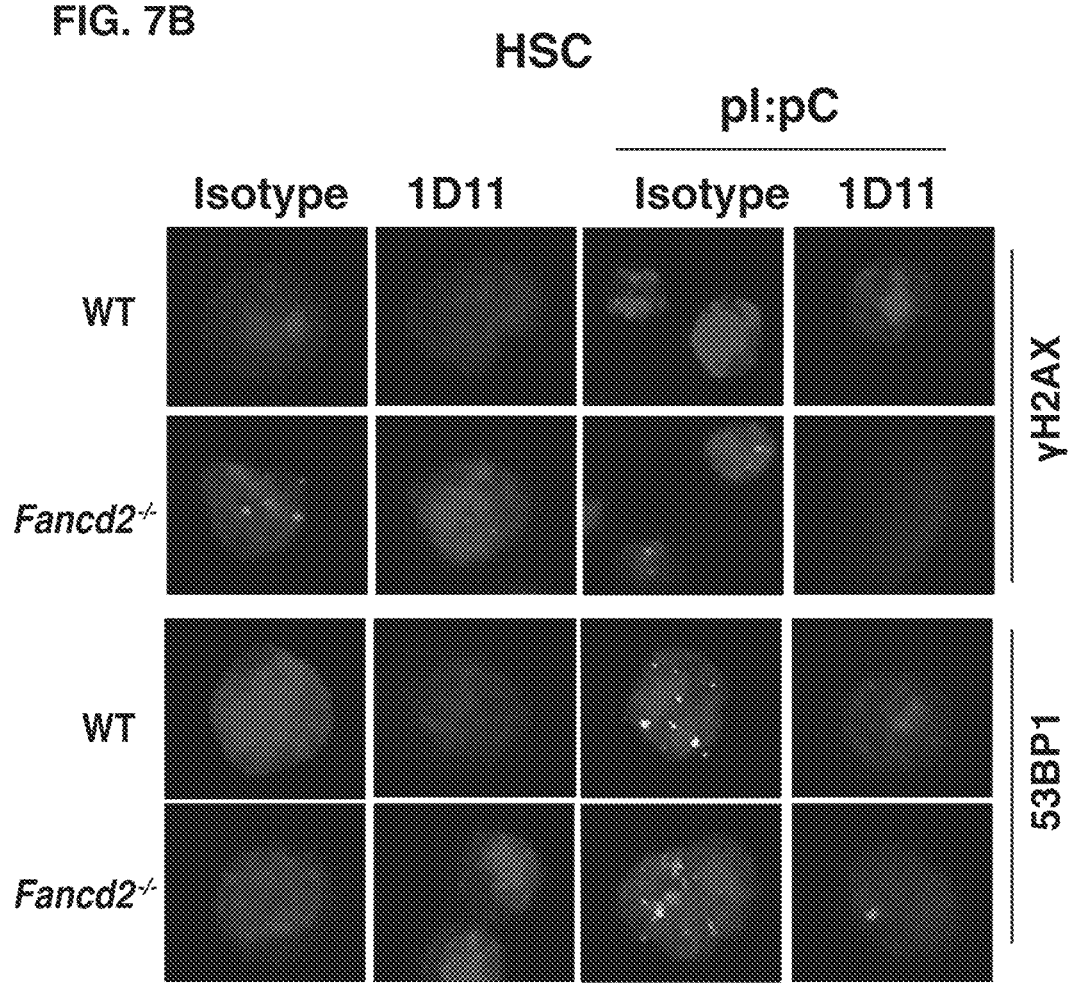
Figure 7C:
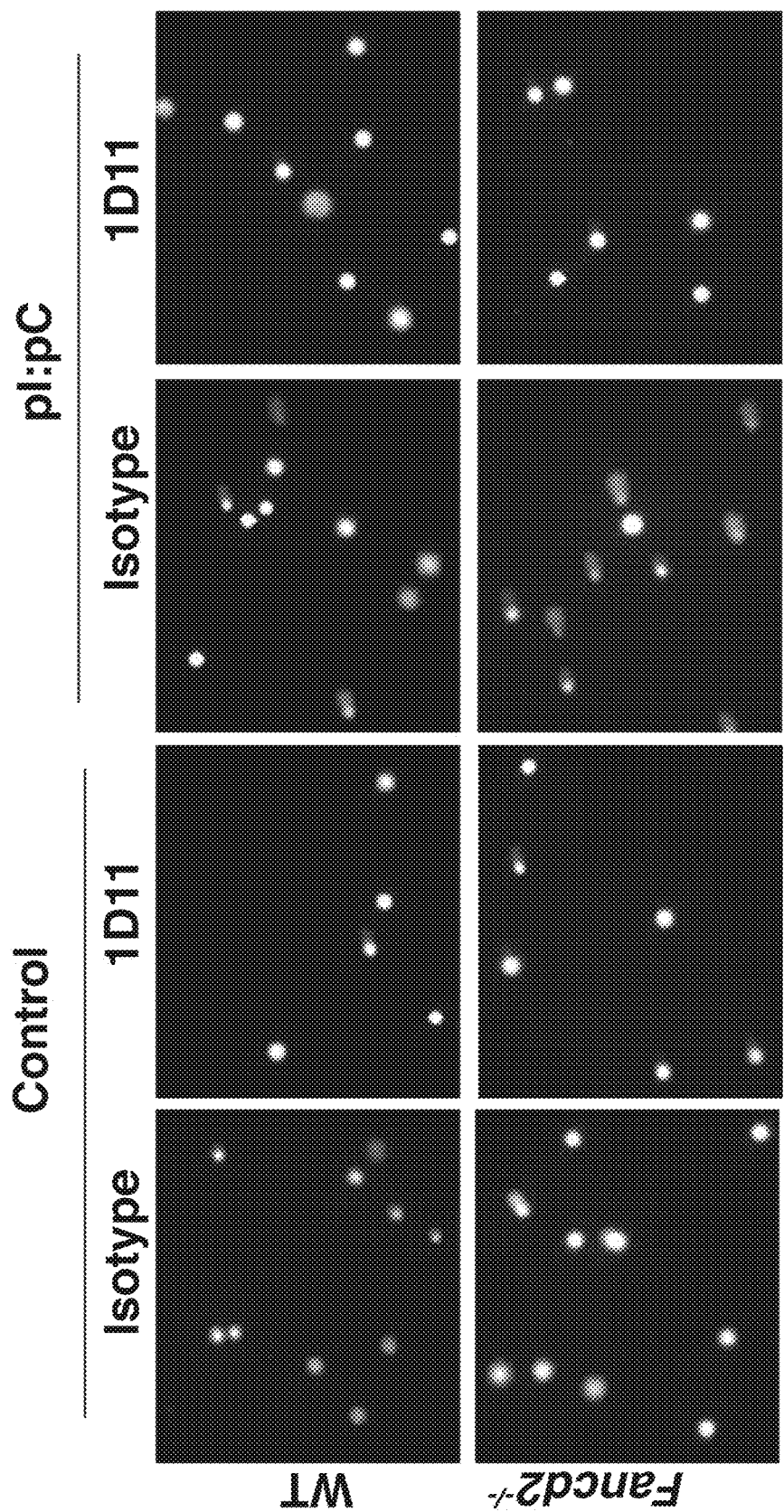
Figure 7D:
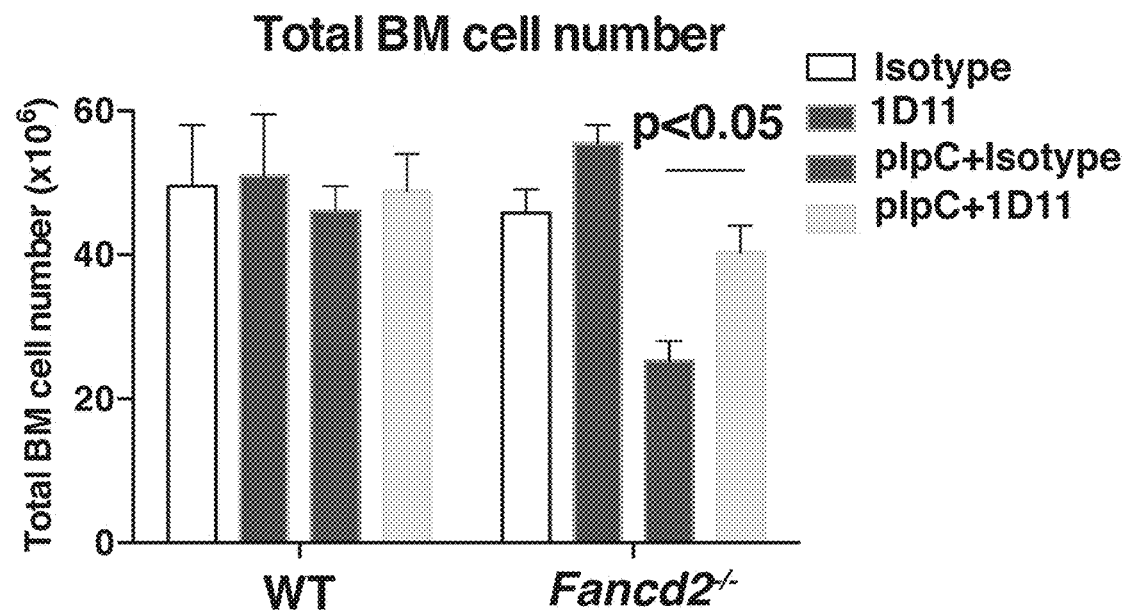
Figure 7E:
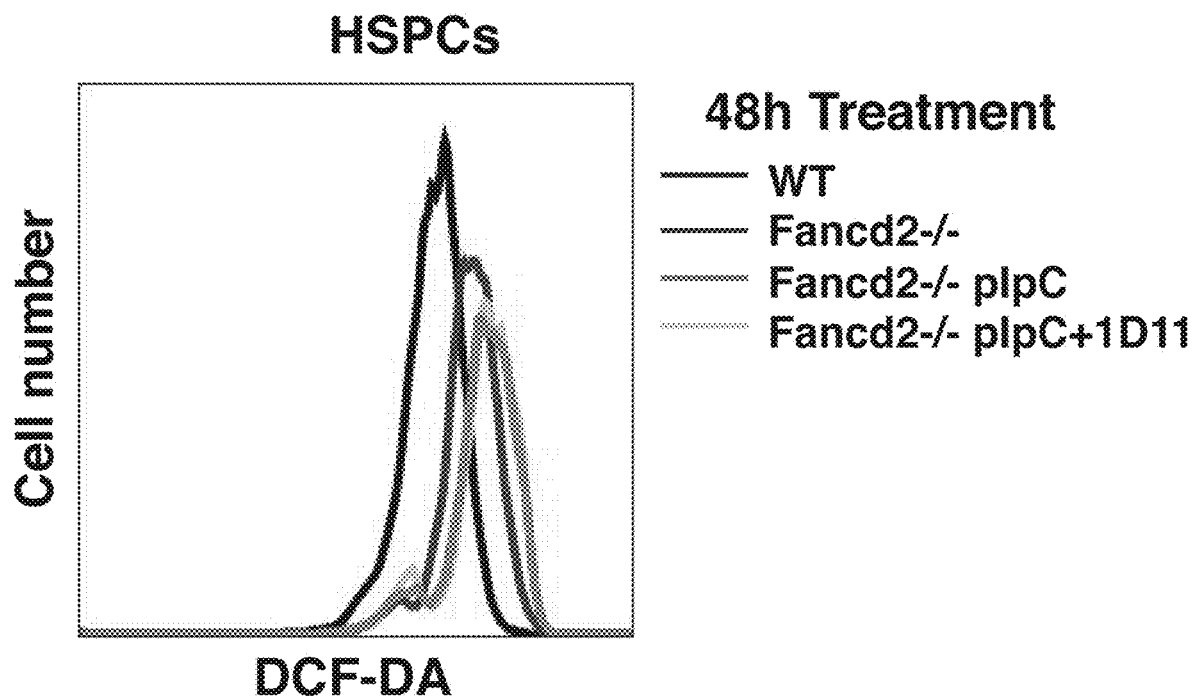
Figure 7F:
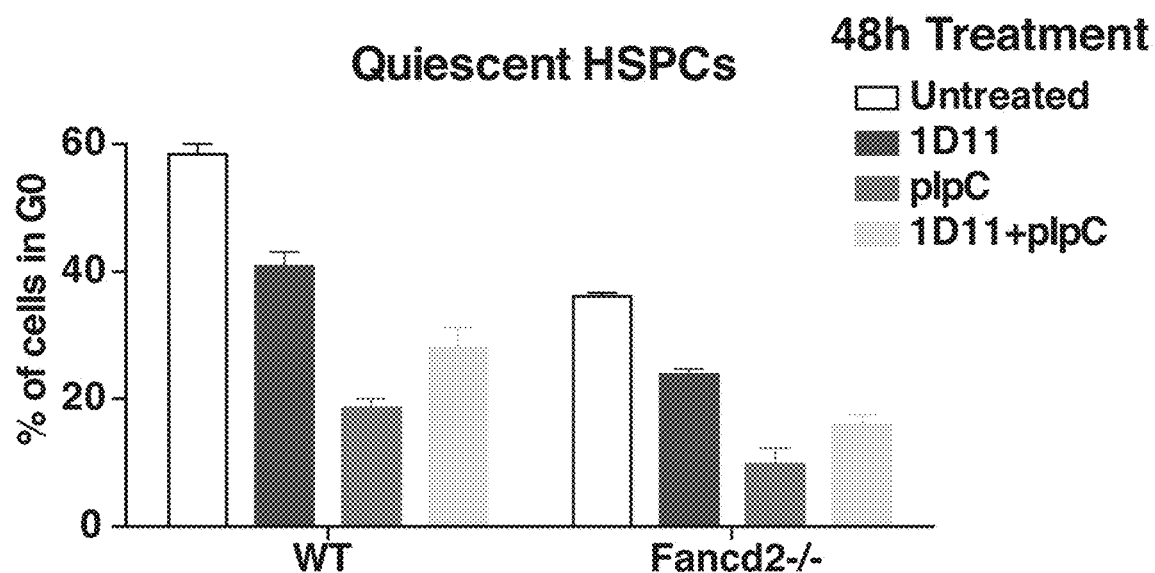

Example 4: Inhibition of TGF-Β Pathway Rescues Physiological Stress-Induced Bone Marrow Failure in FA Mice Physiological stress-induced DNA damage is a source of DNA damage in HSCs in FA. The accumulation of physiological stress-induced DNA damage results in a collapse of the hematopoietic system in a murine FA model (Walter et al., 2015). Interestingly, polyinosinic:polycytidylic acid (pI:pC) exposure caused activation of TGF-β pathway in HSPCs (FIG. 7A). To determine whether inhibition of TGF-β pathway also counteracts the genomic instability of HSCs caused by physiological stress, we simultaneously treated WT and Fancd2$^{-/-}$ mice for 48h with pI:pC (to induce stress) and 1D11 (to block the TGF-β pathway). As previously described (Walter et al., 2015), administration of pI:pC induced DNA damage in HSCs and caused increased levels of γH2AX and 53BP1 foci (FIGS. 1A-1D and 7B); inhibition of the TGF-β pathway by 1D11 markedly reduced the pI:pC-induced DNA damage (FIGS. 1A-4D, 7B, and 7C). Importantly, inhibition of the TGF-β pathway rescued the viability of Fancd2$^{-/-}$ total bone marrow cells following pI:pC treatment (FIG. 7D). Consistent with the previous study (Walter et al., 2015), pI:pC exposure induced oxidative stress in HSPCs from Fancd2$^{-/-}$ mice, however, 1D11 did not affect the level of oxidative stress (FIG. 7E). As expected, pI:pC exposure induced proliferation of HSPCs, resulting in a concomitant reduction in the frequencies of quiescent cells. Interestingly, 1D11 treatment reduced pI:pC-induced cell cycling and increased the percentage of quiescent HSPCs, perhaps accounting for the improved DNA repair (FIG. 7F). Thus, TGF-β pathway inhibition counteracts physiological stress-induced DNA damage in HSCs.

Figure 7G:
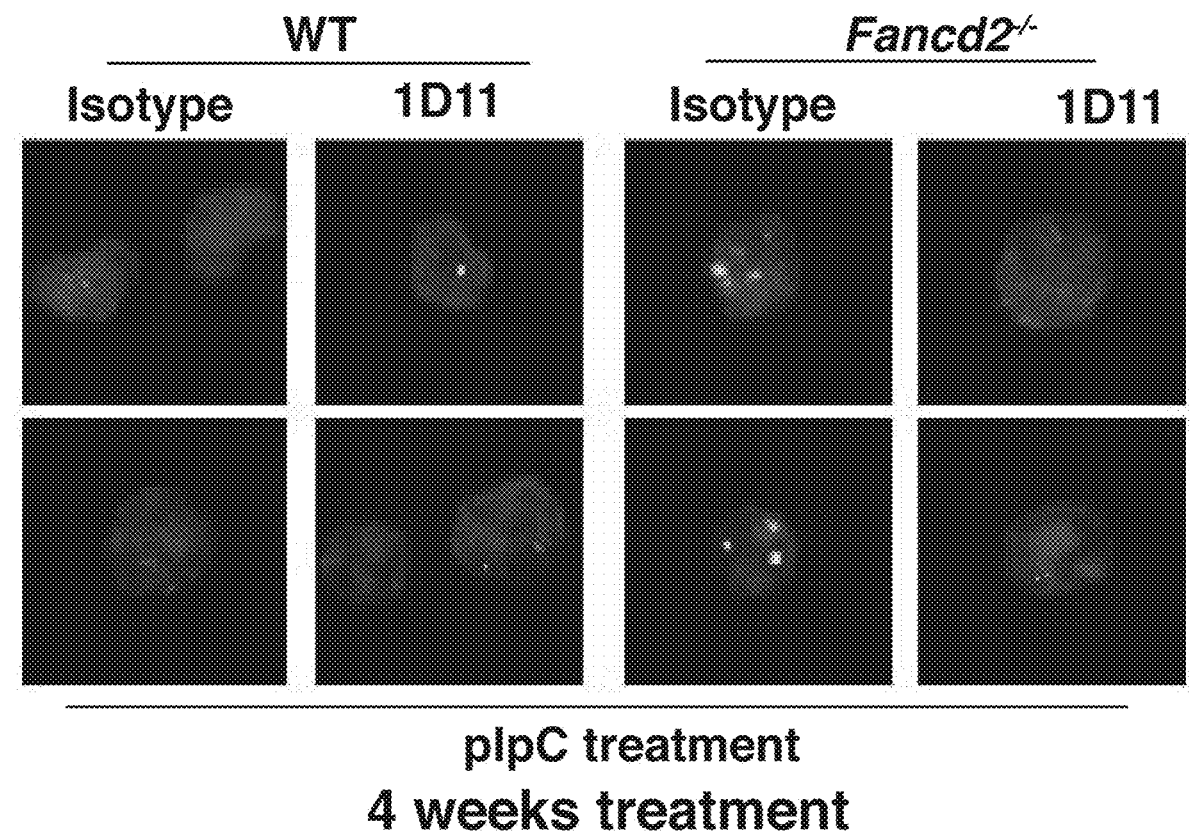

To determine whether TGF-β pathway inhibition rescues pI:pC induced bone marrow failure, we treated WT and Fancd2$^{-/-}$ mice with pI:pC and 1D11 (FIG. 1E). Interestingly, four weeks of pI:pC treatment caused peripheral blood pancytopenia in isotype control antibody-treated Fancd2$^{-/-}$ mice with reduction in red blood cells (RBC), white blood cells (WBC) and hemoglobin levels (FIG. 1F). However, administration of 1D11 significantly prevented these peripheral blood abnormalities (FIG. 1F). To examine the bone marrow HSC function, we next transplanted bone marrow cells from these pI:pC (plus or minus 1D11) treated donor mice into lethally irradiated recipients and evaluated spleen colony-forming units (CFU-S), thus allowing the quantification of the surviving multipotent short-term HSCs. As expected, pI:pC treatment caused a marked reduction in the CFU-S content of Fancd2$^{-/-}$ bone marrow, and 1D11 improved this defect (FIG. 1G). Consistent with these results, in a competitive repopulation experiment, recipient mice transplanted with bone marrow from 1D11 treated Fancd2-/- mice showed improved short-term donor cell engraftment compared to the recipients transplanted with isotype control (FIG. 1H). Bone marrow HSPCs from Fancd2$^{-/-}$ mice treated with 1D11 also exhibited less DNA damage upon pI:pC exposure (FIGS. 1I, 1J, and 7G). Together, these data suggest that TGF-β pathway inhibition rescues pI:pC-induced bone marrow failure in FA mice and may be effective in preventing the bone marrow collapse of FA patients observed after viral infections.

Figure 5A:
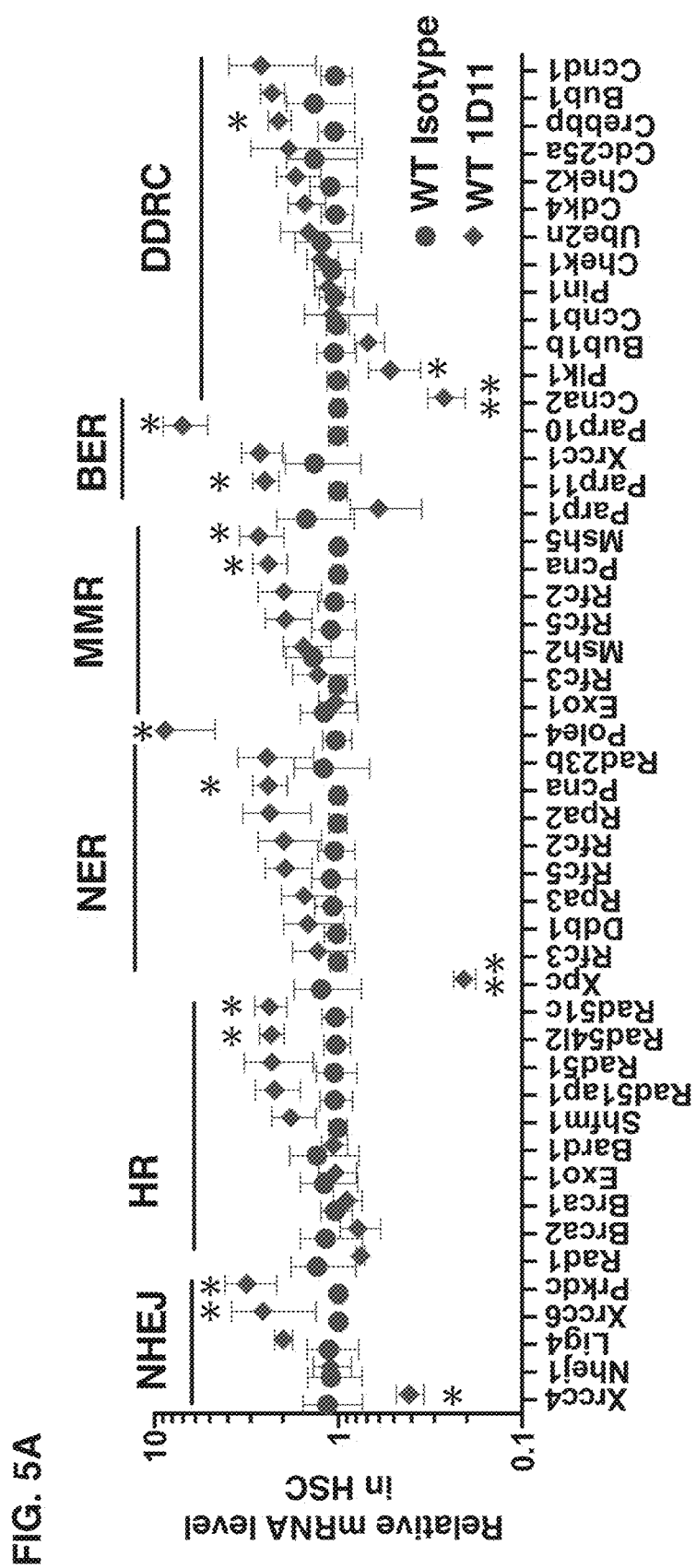
Figure 5B:
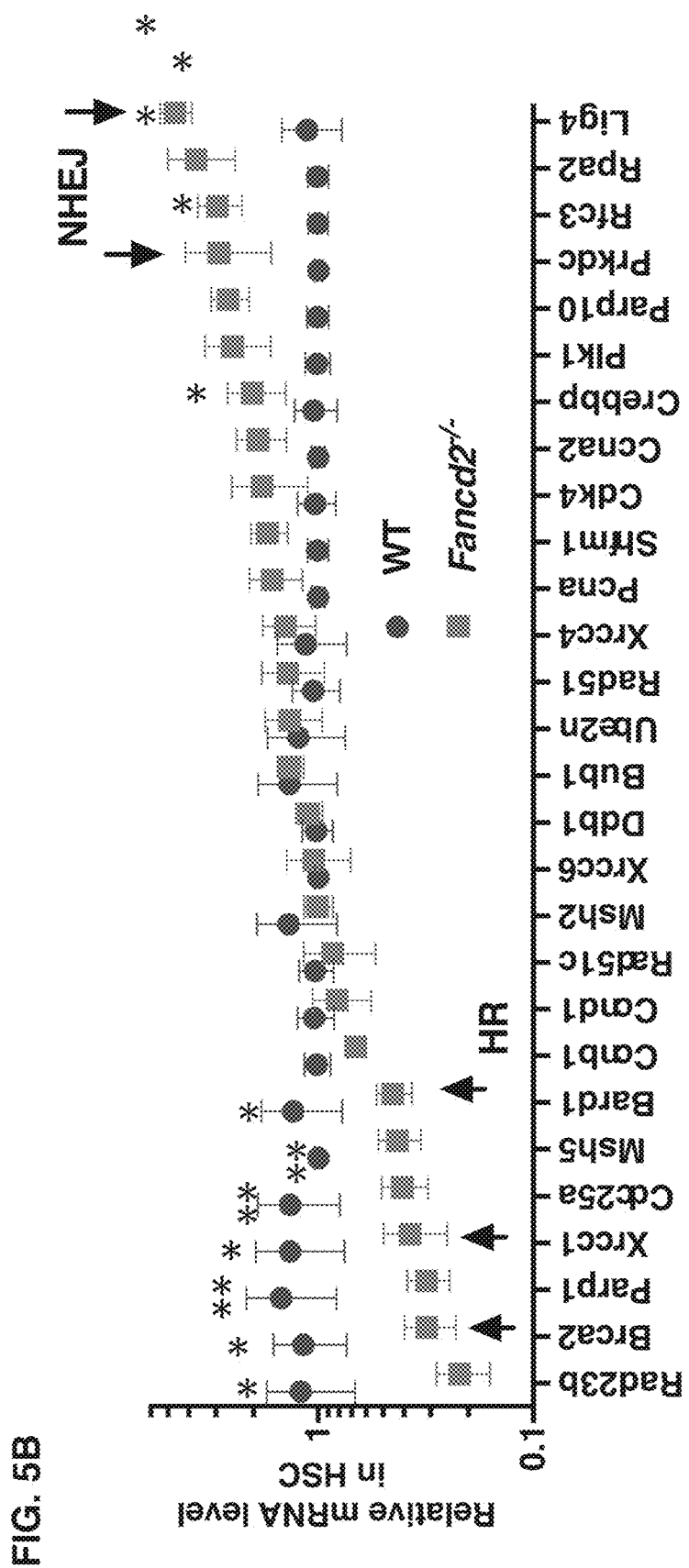
Figure 5C:
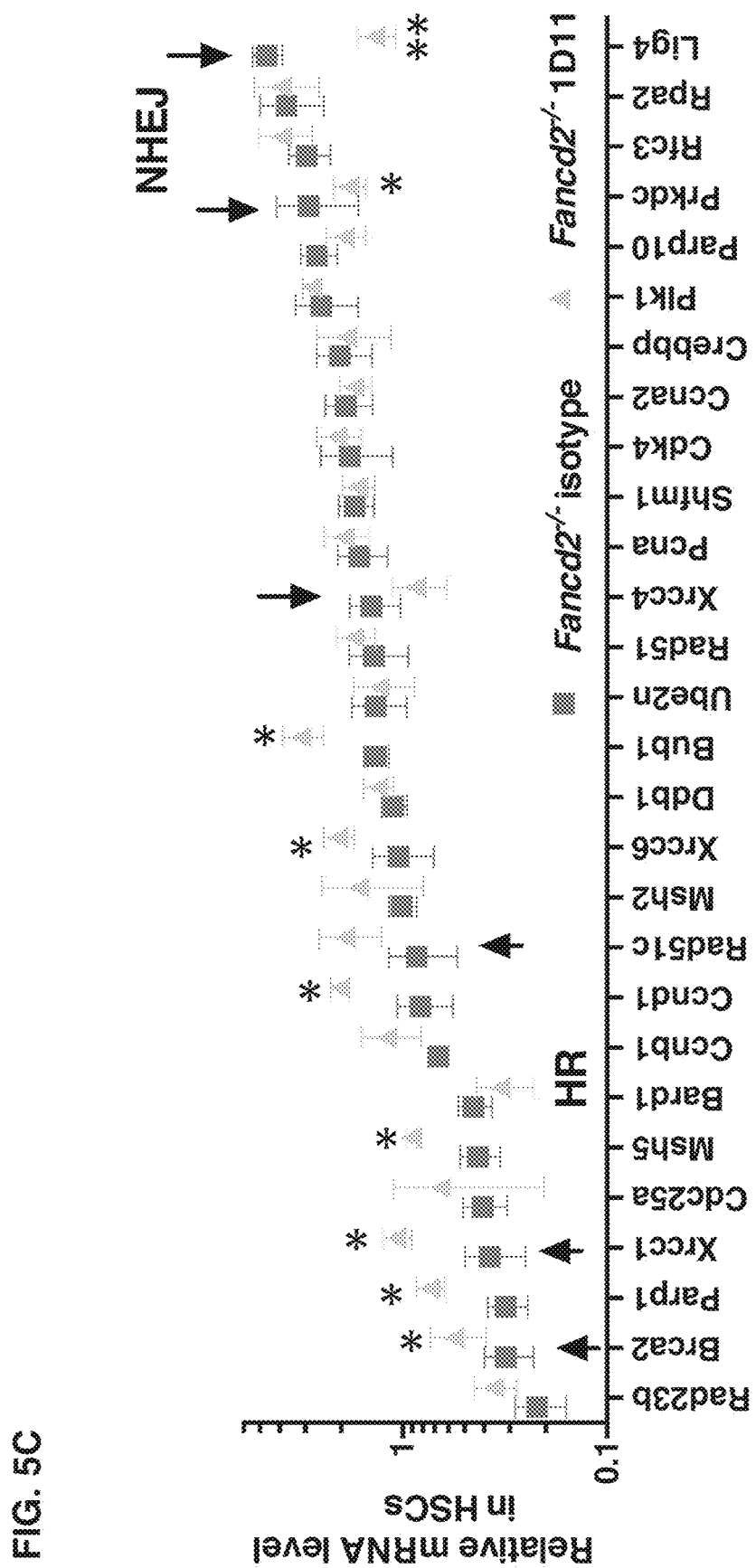
Figure 5D:
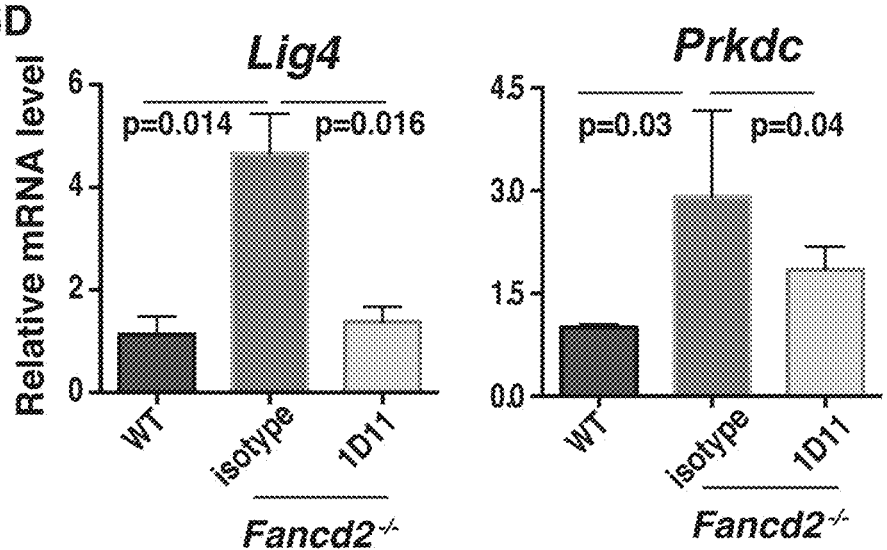
Figure 5E:
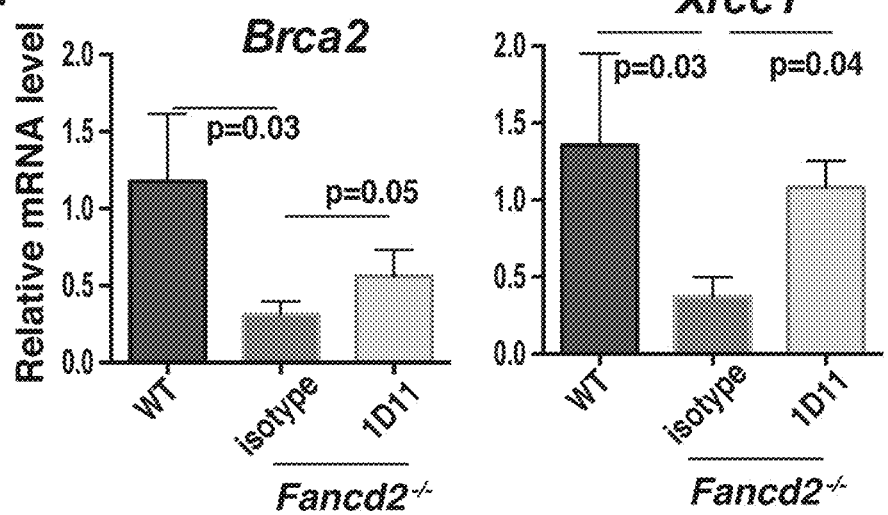
Figure 5F:
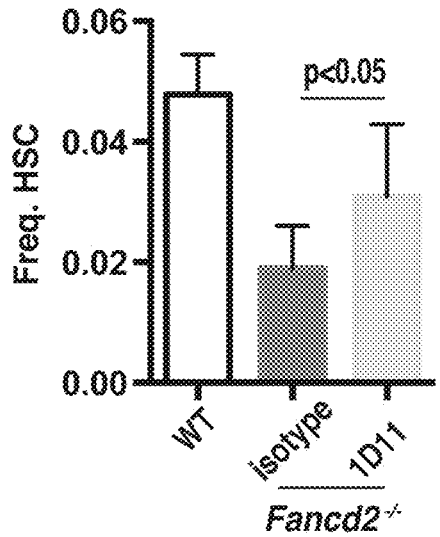
Figure 5G:
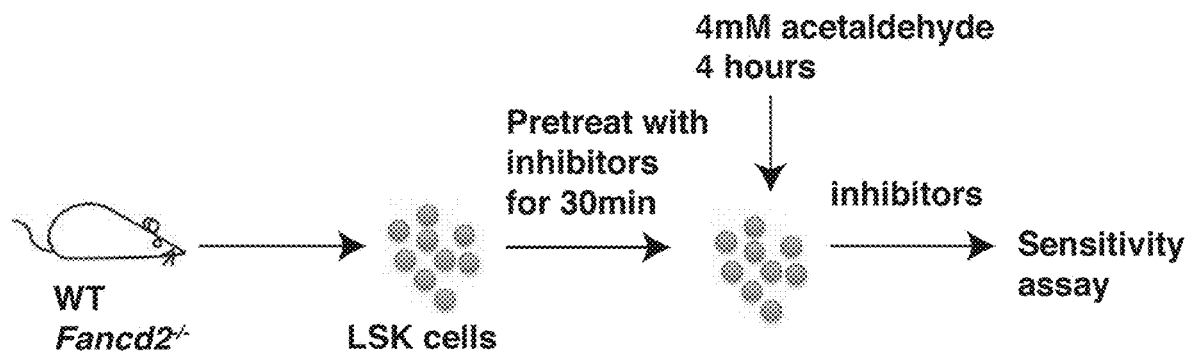
Figure 5H:
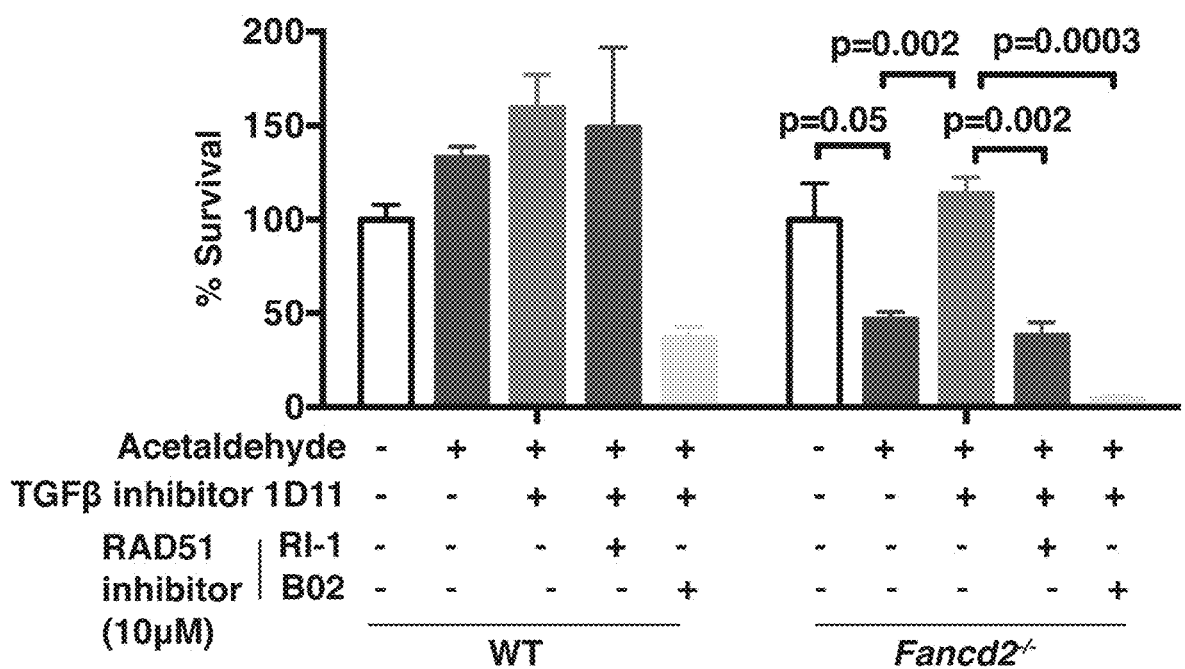
Figure 8A:
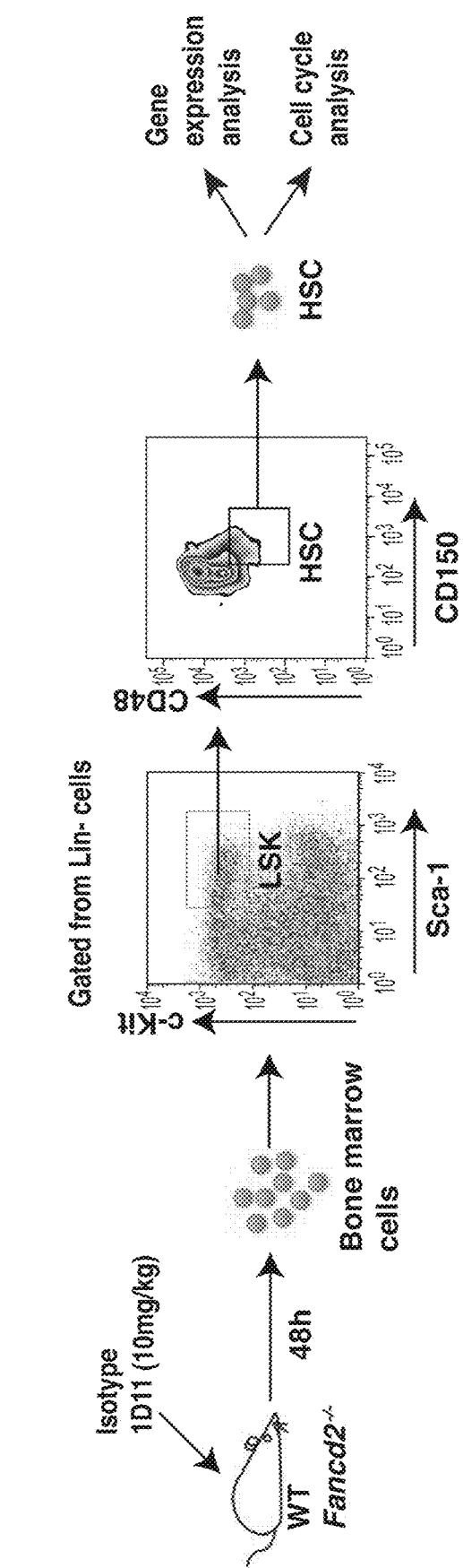
Figure 8B:
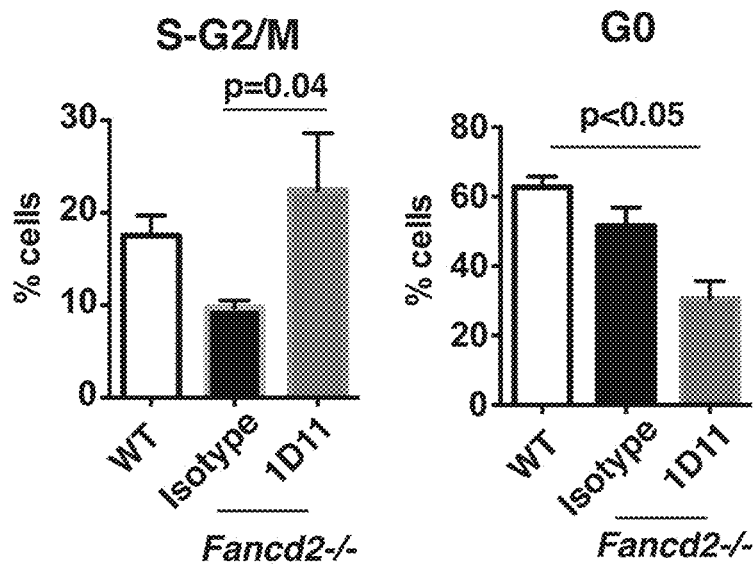
Figure 8C:
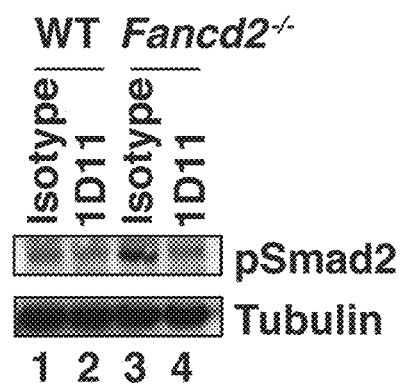
Figure 8D:
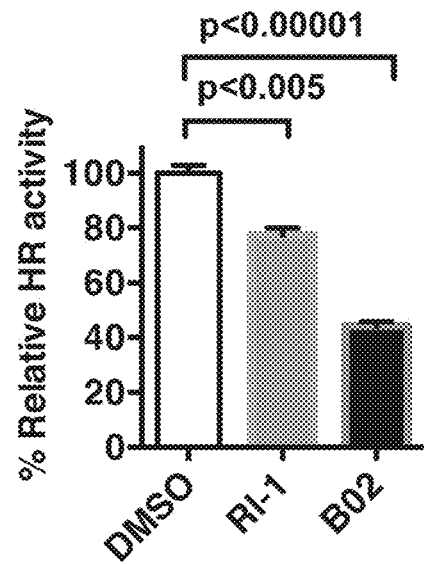
Figure 8E:
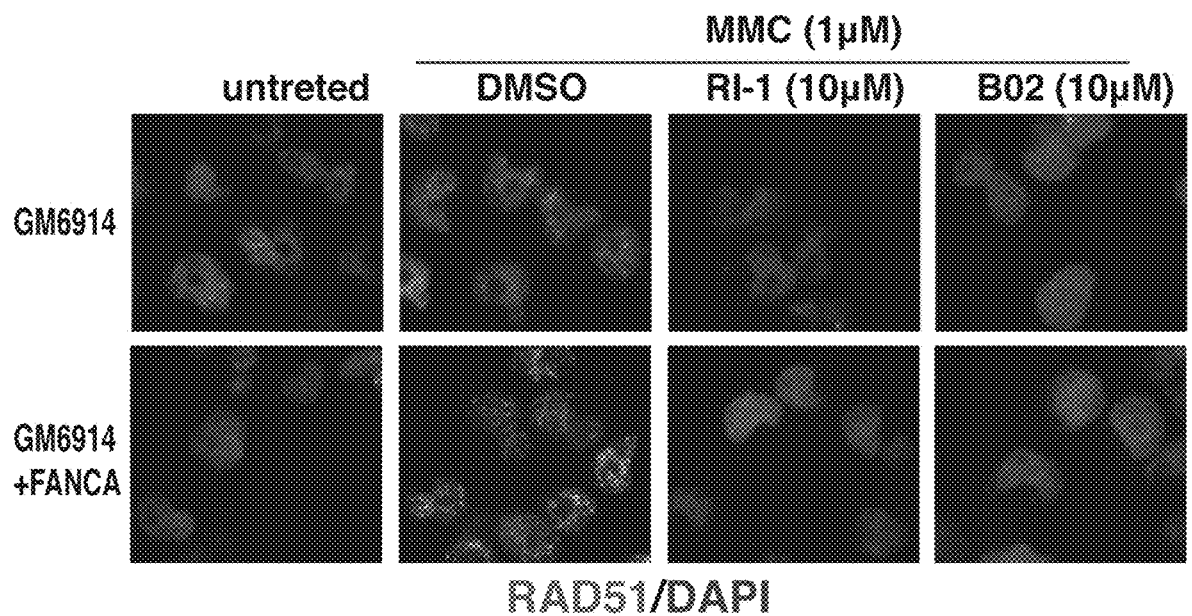
Figure 8F:
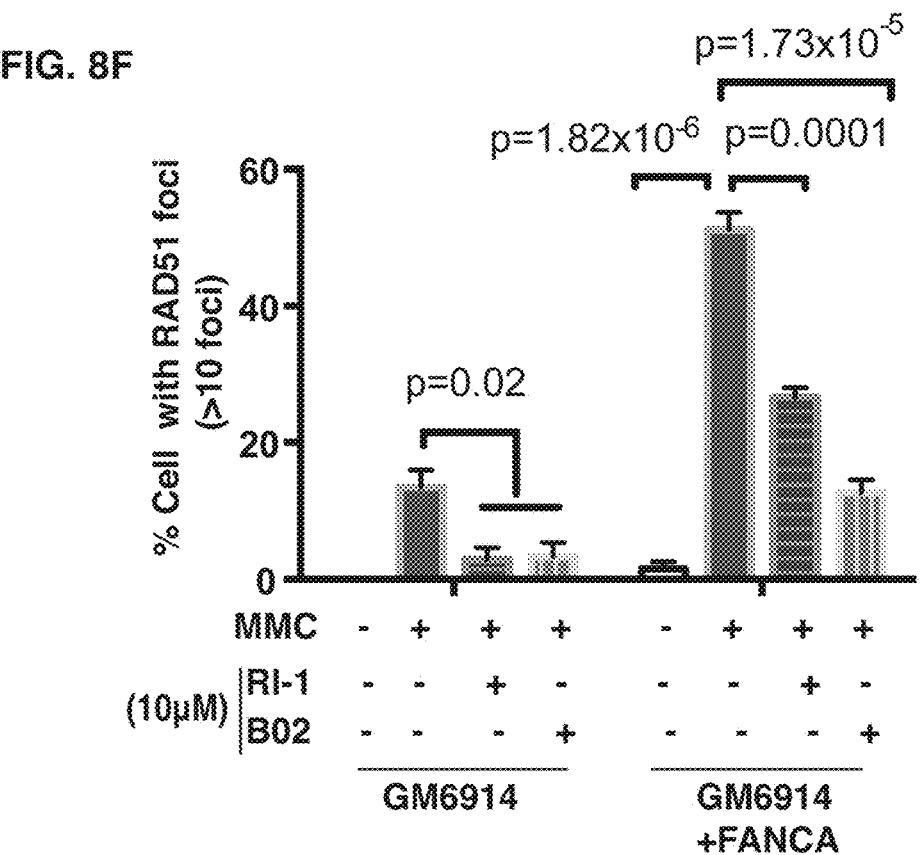
Figure 8G:
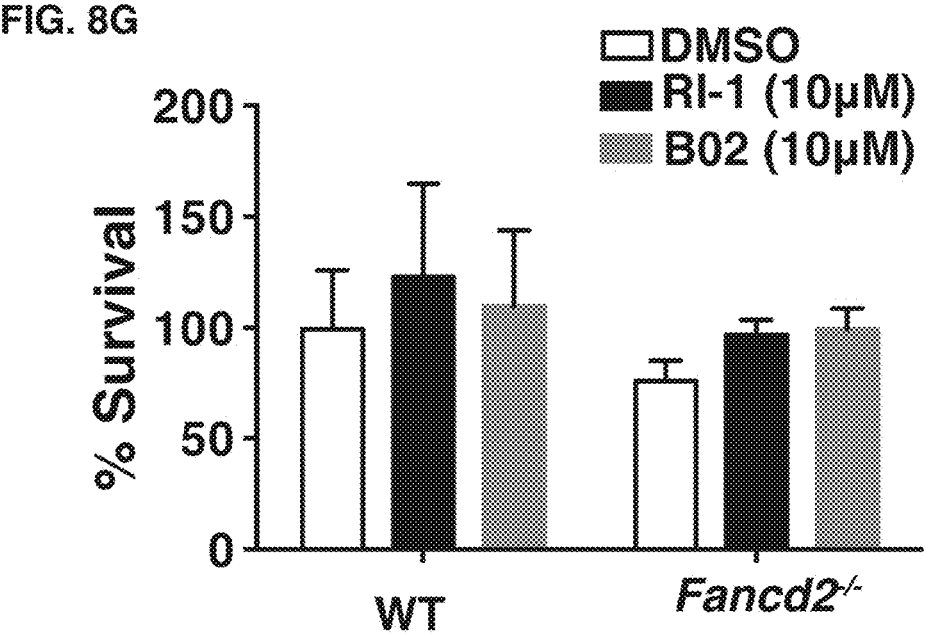
Figure 8H:
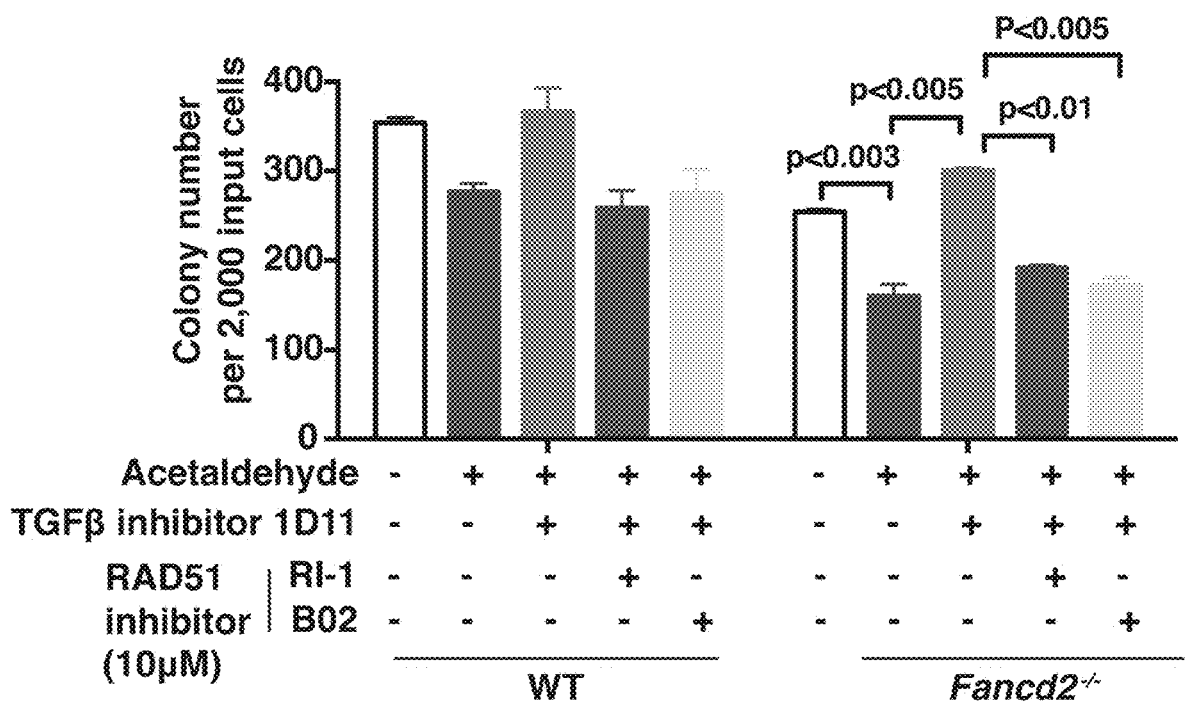

Example 5: TGF-B Pathway Inhibition Upregulates HR and Downregulates NHEJ in HSCs of FA Mice To determine the molecular mechanism by which TGF-β pathway regulates DNA repair and rescues genotoxicity in HSCs, we next analyzed the expression of DNA repair genes in HSCs. Genes associated with NHEJ, HR, nucleotide excision repair (NER), mismatch repair (MMR), and the DNA damage response (DDR) were evaluated. Interestingly, over 70% of DNA repair genes examined were significantly upregulated in HSCs from WT mice exposed to 1D11, the neutralizing anti-murine TGF-β monoclonal antibody (FIGS. 6A and 8A). In contrast, many genes involved in NHEJ were upregulated and many genes involved in HR were downregulated in HSCs from Fancd2$^{-/-}$ mice, when compared to WT HSCs (FIG. 5B). This skewed expression pattern in Fancd2$^{-/-}$ HSCs was reversed by TGF-β pathway inhibition, as 1D11 antibody treatment induced expression of HR genes such as Brca2 and Xrcc1 in Fancd2$^{-/-}$ HSCs, and caused a concomitant reduction of NHEJ gene expression, such as Lig4 and Prkdc (FIG. 5C-5E). Previous studies have shown that HR is upregulated when HSCs are driven into the cell cycle, thereby resulting in repair of double strand breaks (Beerman et al., 2014). Accordingly, the increase in HR activity in FA HSCs following TGF-β pathway inhibition may result, at least in part, from the release from cell cycle arrest (FIG. 8B), subsequently leading to a higher frequency of HSCs in FA mice (FIG. 5F). To confirm that inhibition of TGF-β pathway in HSCs creates an HR-competent state and thereby functionally protects them from genotoxicity, we inhibited both HR and TGF-β pathway and examined the survival of cells after acetaldehyde exposure (FIG. 5G). We used pharmacologic inhibitors which blocked HR, resulting in the reduction of RAD51 foci and the inhibition of DR-GFP plasmid recombination in a reporter assay (FIG. 8D-8F). As expected, 1D11 exposure inhibited TGF-β pathway signaling in bone marrow from FA mice (FIG. 8C). Interestingly, 1D11 did not protect the HSPCs from acetaldehyde-induced genotoxicity when HR was inhibited by pharmacologic inhibitors of RAD51 (Budke et al., 2012; Huang et al., 2012) (FIGS. 5H, 8G and 8H). Collectively, these data indicate that TGF-β pathway inhibition upregulates HR and downregulates NHEJ in HSPCs of Fancd2$^{-/-}$ mice and functionally promotes their survival.

REFERENCES

1. Shimamura, A. & Alter, B. P. Pathophysiology and management of inherited bone marrow failure syndromes. *Blood reviews* 24, 101-122 (2010).
2. Kottemann, M. C. & Smogorzewska, A. Fanconi anaemia and the repair of Watson and Crick DNA crosslinks. *Nature* 493, 356-363 (2013).
3. Deans, A. J. & West, S. C. DNA interstrand crosslink repair and cancer. *Nat Rev Cancer* 11, 467-480 (2011).
4. Chan, K. L., Palmai-Pallag, T., Ying, S. & Hickson, I. D. Replication stress induces sister-chromatid bridging at fragile site loci in mitosis. *Nat Cell Biol* 11, 753-760 (2009).
5. Naim, V. & Rosselli, F. The FANC pathway and BLM collaborate during mitosis to prevent micro-nucleation and chromosome abnormalities. *Nat Cell Biol* 11, 761-768 (2009).
6. Vinciguerra, P., Godinho, S. A., Parmar, K., Pellman, D. & D'Andrea, A. D. Cytokinesis failure occurs in Fanconi anemia pathway-deficient murine and human bone marrow hematopoietic cells. *J Clin Invest* 120, 3834-3842 (2010).
7. Pang, Q. & Andreassen, P. R. Fanconi anemia proteins and endogenous stresses. *Mutat Res* 668, 42-53 (2009).
8. Dufour, C., et al. TNF-alpha and IFN-gamma are over-expressed in the bone marrow of Fanconi anemia patients and TNF-alpha suppresses erythropoiesis in vitro. *Blood* 102, 2053-2059 (2003).
9. Ceccaldi, R., et al. Bone marrow failure in Fanconi anemia is triggered by an exacerbated p53/p21 DNA damage response that impairs hematopoietic stem and progenitor cells. *Cell stem cell* 11, 36-49 (2012).
10. Crossan, G. P., et al. Disruption of mouse Slx4, a regulator of structure-specific nucleases, phenocopies Fanconi anemia. *Nature genetics* 43, 147-152 (2011).
11. Pulliam-Leath, A. C., et al. Genetic disruption of both Fancc and Fancg in mice recapitulates the hematopoietic manifestations of Fanconi anemia. *Blood* 116, 2915-2920 (2010).
12. Parmar, K., et al. Hematopoietic stem cell defects in mice with deficiency of Fancd2 or Usp1. *Stem Cells* 28, 1186-1195 (2010).
13. Zhang, Q. S., et al. Fancd2-/- mice have hematopoietic defects that can be partially corrected by resveratrol. *Blood* 116, 5140-5148 (2010).
14. Tulpule, A., et al. Knockdown of Fanconi anemia genes in human embryonic stem cells reveals early developmental defects in the hematopoietic lineage. *Blood* 115, 3453-3462 (2010).
15. Ito, K., et al. Reactive oxygen species act through p38 MAPK to limit the lifespan of hematopoietic stem cells. *Nature medicine* 12, 446-451 (2006).
16. Ruzankina, Y., et al. Deletion of the developmentally essential gene ATR in adult mice leads to age-related phenotypes and stem cell loss. *Cell stem cell* 1, 113-126 (2007).
17. Niedernhofer, L. J. DNA repair is crucial for maintaining hematopoietic stem cell function. *DNA Repair (Amst)* 7, 523-529 (2008).
18. Mohrin, M., et al. Hematopoietic stem cell quiescence promotes error-prone DNA repair and mutagenesis. *Cell stem cell* 7, 174-185 (2010).
19. Milyaysky, M., et al. A distinctive DNA damage response in human hematopoietic stem cells reveals an apoptosis-independent role for p53 in self-renewal. *Cell stem cell* 7, 186-197 (2010).

20. Seita, J., Rossi, D. J. & Weissman, I. L. Differential DNA damage response in stem and progenitor cells. *Cell stem cell* 7, 145-147 (2010).
21. Brenet, F., Kermani, P., Spektor, R., Rafii, S. & Scandura, J. M. TGFbeta restores hematopoietic homeostasis after myelosuppressive chemotherapy. *J Exp Med* 210, 623-639 (2013).
22. Zhou, L., et al. Reduced SMAD7 leads to overactivation of TGF-beta signaling in MDS that can be reversed by a specific inhibitor of TGF-beta receptor I kinase. *Cancer Res* 71, 955-963 (2011).
23. Zingariello, M., et al. Characterization of the TGF-beta1 signaling abnormalities in the Gatallow mouse model of myelofibrosis. *Blood* 121, 3345-3363 (2013).
24. Ikushima, H. & Miyazono, K. TGFbeta signalling: a complex web in cancer progression. *Nat Rev Cancer* 10, 415-424 (2010).
25. Cron, K R., et al. Proteasome inhibitors block DNA repair and radiosensitize non-small cell lung cancer. *PLoS One* 8, e73710 (2013).
26. Zhou, L., et al. Inhibition of the TGF-beta receptor I kinase promotes hematopoiesis in MDS. *Blood* 112, 3434-3443 (2008).
27. Jinnin, M., Ihn, H. & Tamaki, K. Characterization of SIS3, a novel specific inhibitor of Smad3, and its effect on transforming growth factor-beta1-induced extracellular matrix expression. *Molecular pharmacology* 69, 597-607 (2006).
28. Garaycoechea, J. I., et al. Genotoxic consequences of endogenous aldehydes on mouse haematopoietic stem cell function. *Nature* 489, 571-575 (2012).
29. Li, Y., et al. Mesenchymal stem/progenitor cells promote the reconstitution of exogenous hematopoietic stem cells in Fancg−/− mice in vivo. *Blood* 113, 2342-2351 (2009).
30. Epperly, M. W., et al. Increased longevity of hematopoiesis in continuous bone marrow cultures and adipocytogenesis in marrow stromal cells derived from Smad3(−/−) mice. *Exp Hematol* 33, 353-362 (2005).
31. Jessen, W. J., et al. MEK inhibition exhibits efficacy in human and mouse neurofibromatosis tumors. *J Clin Invest* 123, 340-347 (2013).
32. Langevin, F., Crossan, G. P., Rosado, I. V., Arends, M. J. & Patel, K. J. Fancd2 counteracts the toxic effects of naturally produced aldehydes in mice. *Nature* 475, 53-58 (2011).
33. Kirshner, J., et al. Inhibition of transforming growth factor-beta1 signaling attenuates ataxia telangiectasia mutated activity in response to genotoxic stress. *Cancer Res* 66, 10861-10869 (2006).
34. Kennedy, R. D., et al. Fanconi anemia pathway-deficient tumor cells are hypersensitive to inhibition of ataxia telangiectasia mutated. *J Clin Invest* 117, 1440-1449 (2007).
35. Ichida, J. K., et al. A small-molecule inhibitor of tgf-Beta signaling replaces sox2 in reprogramming by inducing nanog. *Cell stem cell* 5, 491-503 (2009).
36. Lin, T., et al. A chemical platform for improved induction of human iPSCs. *Nat Methods* 6, 805-808 (2009).
37. Wu, J. H. & Jones, N.J. Assessment of DNA interstrand crosslinks using the modified alkaline comet assay. *Methods Mol Biol* 817, 165-181 (2012).
38. McKenna, D. J., Gallus, M., McKeown, S. R., Downes, C. S. & McKelvey-Martin, V. J. Modification of the alkaline Comet assay to allow simultaneous evaluation of mitomycin C-induced DNA cross-link damage and repair of specific DNA sequences in RT4 cells. *DNA Repair (Amst)* 2, 879-890 (2003).
39. Nakanishi, K., et al. Human Fanconi anemia monoubiquitination pathway promotes homologous DNA repair. *Proceedings of the National Academy of Sciences of the United States of America* 102, 1110-1115 (2005).
40. Mansour, W. Y., et al. Hierarchy of nonhomologous end-joining, single-strand annealing and gene conversion at site-directed DNA double-strand breaks. *Nucleic acids research* 36, 4088-4098 (2008).
41. Adamo, A., et al. Preventing nonhomologous end joining suppresses DNA repair defects of Fanconi anemia. *Mol Cell* 39, 25-35 (2010).
42. Pace, P., et al. Ku70 corrupts DNA repair in the absence of the Fanconi anemia pathway. *Science* 329, 219-223 (2010).
43. Raaijmakers, M. H., et al. Bone progenitor dysfunction induces myelodysplasia and secondary leukaemia. *Nature* 464, 852-857 (2010).
44. Hanoun, M., et al. Acute myelogenous leukemia-induced sympathetic neuropathy promotes malignancy in an altered hematopoietic stem cell niche. *Cell stem cell* 15, 365-375 (2014).
45. Krause, D. S., et al. Differential regulation of myeloid leukemias by the bone marrow microenvironment. *Nature medicine* 19, 1513-1517 (2013).
46. Pang, Q., et al. The Fanconi anemia protein FANCC binds to and facilitates the activation of STAT1 by gamma interferon and hematopoietic growth factors. *Molecular and cellular biology* 20, 4724-4735 (2000).
47. Pang, Q., Keeble, W., Christianson, T. A., Faulkner, G. R. & Bagby, G. C. FANCC interacts with Hsp70 to protect hematopoietic cells from IFN-gamma/TNF-alpha-mediated cytotoxicity. *The EMBO journal* 20, 4478-4489 (2001).
48. Benazet, J. D., et al. Smad4 is required to induce digit ray primordia and to initiate the aggregation and differentiation of chondrogenic progenitors in mouse limb buds. *Development* 139, 4250-4260 (2012).
49. Li, J., et al. TNF-alpha induces leukemic clonal evolution ex vivo in Fanconi anemia group C murine stem cells. *J Clin Invest* 117, 3283-3295 (2007).
50. Bunting, S. F. & Nussenzweig, A. Dangerous liaisons: Fanconi anemia and toxic nonhomologous end joining in DNA crosslink repair. *Mol Cell* 39, 164-166 (2010).
51. Grafe, I., et al. Excessive transforming growth factor-beta signaling is a common mechanism in osteogenesis imperfecta. *Nature medicine* 20, 670-675 (2014).

We claim:

1. A method of treating, preventing or delaying the onset of bone marrow failure in a patient in need thereof, the method comprising administering to the patient a composition comprising fresolimumab, anti-TGFβ antibody 1 D11 (deposited under ATCC Accession No. HB 9849), or an antigen-binding fragment thereof, wherein the patient has Fanconi Anemia (FA) and does not receive a bone marrow transplant.

2. The method of claim 1, wherein the composition is administered when the patient is having medical crisis.

3. The method of claim 2, wherein the medical crisis is an infection.

4. The method of claim 3, wherein the infection is a viral or bacterial infection.

5. The method of claim 1, wherein 0.1 mg/kg to 150 mg/kg of fresolimumab, anti-TGFβ antibody 1 D11, or an antigen-binding fragment thereof is administered.

6. The method of claim 5, wherein 0.5 mg/kg to 10 mg/kg of fresolimumab, anti-TGFβ antibody 1 D11, or an antigen-binding fragment thereof is administered.

7. The method of claim 6, wherein 1 mg/kg to 5 mg/kg of fresolimumab, anti-TGFβ antibody 1 D11, or an antigen-binding fragment thereof is administered.

8. The method of claim 1, wherein the composition is administered one to seven times per week.

9. The method of claim 8, wherein the composition is administered three times per week.

10. The method of claim 8, wherein the composition is administered two times per week.

11. The method of claim 1, wherein the composition is administered for a duration of 1 week to 1 year.

12. The method of claim 11, wherein the composition is administered for a duration of one to two months.

13. The method of claim 1, wherein the composition is administered chronically.

14. The method of claim 1, wherein the composition is administered intravenously.

15. The method of claim 1, further comprising administering to the patient androgen therapy or erythropoietin.

* * * * *